US011776692B2

(12) United States Patent
Miura et al.

(10) Patent No.: US 11,776,692 B2
(45) Date of Patent: Oct. 3, 2023

(54) TRAINING DATA COLLECTION APPARATUS, TRAINING DATA COLLECTION METHOD, PROGRAM, TRAINING SYSTEM, TRAINED MODEL, AND ENDOSCOPIC IMAGE PROCESSING APPARATUS

(71) Applicant: FUJIFILM Corporation, Tokyo (JP)

(72) Inventors: Goro Miura, Kanagawa (JP); Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 560 days.

(21) Appl. No.: 17/089,685

(22) Filed: Nov. 4, 2020

(65) Prior Publication Data

US 2021/0052137 A1   Feb. 25, 2021

Related U.S. Application Data

(63) Continuation of application No. PCT/JP2019/018231, filed on May 7, 2019.

(30) Foreign Application Priority Data

May 28, 2018  (JP) ................................ 2018-101498

(51) Int. Cl.
*A61B 1/00* (2006.01)
*G16H 50/20* (2018.01)
(Continued)

(52) U.S. Cl.
CPC ........... *G16H 50/20* (2018.01); *A61B 1/0005* (2013.01); *A61B 1/000094* (2022.02);
(Continued)

(58) Field of Classification Search
CPC ........ G16H 50/20; G16H 30/20; G16H 30/40; G16H 50/70; A61B 1/000094;
(Continued)

(56) References Cited

U.S. PATENT DOCUMENTS 10,521,909 B2   12/2019   Kikuchi
10,593,430 B2   3/2020   Kondo et al.
(Continued)

FOREIGN PATENT DOCUMENTS

JP   2002336193   11/2002
JP   2007209770   8/2007
(Continued)

OTHER PUBLICATIONS

"Office Action of Japan Counterpart Application" with English translation thereof, dated Sep. 13, 2021, p. 1-p. 6.
(Continued)

*Primary Examiner* — Mekonen T Bekele
(74) *Attorney, Agent, or Firm* — JCIPRNET

(57) ABSTRACT

Provided are a training data collection apparatus, a training data collection method, and a program that easily collect training data for use in training of a model that discriminates a lesion from an endoscopic image, a training system, a trained model, and an endoscopic image processing apparatus. Endoscopic images are associated with respective pieces of findings-diagnosis information. When the endoscopic images and the respective piece of findings-diagnosis information that are associated with each other are recorded in a recording apparatus as training data for use in training of a model that discriminates a lesion from an endoscopic image, the endoscopic images associated with the respective pieces of findings-diagnosis information are classified into corresponding groups of the respective pieces of findings-diagnosis information. The endoscopic images are displayed and switched on a group-by-group basis by using tabs.

20 Claims, 26 Drawing Sheets

(51) Int. Cl.
  *G16H 30/20* (2018.01)
  *G16H 30/40* (2018.01)
  *G06F 18/24* (2023.01)
  *G06F 18/214* (2023.01)
  *G06V 10/764* (2022.01)
  *G06V 10/774* (2022.01)

(52) U.S. Cl.
  CPC ...... *A61B 1/000096* (2022.02); *G06F 18/214* (2023.01); *G06F 18/24* (2023.01); *G06V 10/764* (2022.01); *G06V 10/774* (2022.01); *G16H 30/20* (2018.01); *G16H 30/40* (2018.01)

(58) Field of Classification Search
  CPC . A61B 1/000096; A61B 1/0005; A61B 1/045; G06F 18/214; G06F 18/24; G06V 10/764; G06V 10/774; G06V 2201/031; G02B 23/2484
  See application file for complete search history.

(56) References Cited

U.S. PATENT DOCUMENTS

| | | | |
|---|---|---|---|
| 2014/0101080 A1 | 4/2014 | Lee et al. | |
| 2016/0350912 A1 | 12/2016 | Koide et al. | |
| 2017/0091413 A1* | 3/2017 | Kondo | G16H 50/20 |
| 2020/0176123 A1 | 6/2020 | Kondo et al. | |
| 2022/0000351 A1* | 1/2022 | Yamada | G16H 30/40 |

FOREIGN PATENT DOCUMENTS

| | | |
|---|---|---|
| JP | 2015146970 | 8/2015 |
| JP | 2017068838 | 4/2017 |
| JP | 2017189390 | 10/2017 |

OTHER PUBLICATIONS

"International Search Report (Form PCT/ISA/210)" of PCT/JP2019/018231, dated Jul. 23, 2019, with English translation thereof, pp. 1-4.

"Written Opinion of the International Searching Authority (Form PCT/ISA/237)" of PCT/JP2019/018231, dated Jul. 23, 2019, with English translation thereof, pp. 1-7.

"Search Report of Europe Counterpart Application", dated Jun. 21, 2021, p. 1-p. 10.

Spiros V. Georgakopoulos et al., "Weakly-supervised Convolutional Learning for Detection of Inflammatory Gastrointestinal Lesions," 2016 IEEE International Conference on Imaging Systems and Techniques (IST), Oct. 2016, pp. 1-5.

Bernd Münzer et al., "Content-based processing and analysis of endoscopic images and videos: A survey," Multimedia Tools and Applications, vol. 77, Jan. 2017, pp. 1-40.

Younghak Shin et al., "Comparison of hand-craft feature based SVM and CNN based deep learning framework for automatic polyp classification," 2017 39th Annual International Conference of the IEEE Engineering in Medicine and Biology Society (EMBC), Jul. 2017, pp. 3277-3280.

* cited by examiner

TRAINING DATA COLLECTION APPARATUS, TRAINING DATA COLLECTION METHOD, PROGRAM, TRAINING SYSTEM, TRAINED MODEL, AND ENDOSCOPIC IMAGE PROCESSING APPARATUS

CROSS-REFERENCE TO RELATED APPLICATIONS

The present application is a Continuation of PCT International Application No. PCT/JP2019/018231 filed on May 7, 2019 claiming priority under 35 U.S.C § 119(a) to Japanese Patent Application No. 2018-101498 filed on May 28, 2018. Each of the above applications is hereby expressly incorporated by reference, in its entirety, into the present application.

BACKGROUND OF THE INVENTION

1. Field of the Invention

The present invention relates to a training data collection apparatus, a training data collection method, a program, a training system, a trained model, and an endoscopic image processing apparatus and, more particularly, to a technique for discriminating a lesion from an endoscopic image.

2. Description of the Related Art

There are endoscopy filing systems that store endoscopic images and endoscopy management systems that store endoscopic examination information, patient information, and endoscopic images in the market. Further, studies are conducted to implement the practical use of endoscopic computer-aided diagnosis (CAD) systems that detect a lesion or discriminate a lesion during an endoscopic examination.

JP2017-068838A describes a classifier for classifying image feature sets each corresponding to one of regions of interest in medical images into a plurality of imaging findings.

SUMMARY OF THE INVENTION

JP2017-068838A describes a technique of extracting image feature sets from several hundreds to several thousands of images collected in advance for each of ten imaging findings predetermined by a diagnostic radiologist and of generating the classifier by training the classifier using the extracted image feature sets.

In addition, to train an artificial intelligence (AI) engine to be mounted in an endoscopic CAD system, a doctor needs to acquire images of lesions, findings-diagnosis information obtained at the time of capturing of the images of lesions, examination moving images recorded during endoscopic examinations, and so on separately from individual systems such as an endoscopy management system and an endoscopy filing system and convert them into a format usable for training of the AI.

As described above, it is necessary to collect a vast amount of training data of medical cases or the like to train a model. There is a problem in that collecting a vast amount of training data requires lots of work.

The present invention is made in view of such a circumstance, and it is an object of the present invention to provide a training data collection apparatus, a training data collection method, and a program that easily collect training data for use in training of a model that discriminates a lesion from an endoscopic image, and to provide a training system, a trained model, and an endoscopic image processing apparatus.

To accomplish the above object, a training data collection apparatus according to one aspect is a training data collection apparatus including: a display control unit that causes one or a plurality of endoscopic images captured with an endoscope to be displayed in an image display area of a display device and that causes one or a plurality of pieces of findings-diagnosis information on a lesion to be displayed in a findings-diagnosis information display area of the display device; an accepting unit that accepts an operation on an input device, the operation being an operation of selecting at least one endoscopic image from among the endoscopic images displayed in the image display area and a piece of findings-diagnosis information relating to the at least one endoscopic image from among the pieces of findings-diagnosis information displayed in the findings-diagnosis information display area; an associating unit that associates the selected endoscopic image with the selected piece of findings-diagnosis information; and a recording control unit that causes a recording apparatus to record therein, as training data for use in training of a model that discriminates a lesion from an endoscopic image, the endoscopic image and the piece of findings-diagnosis information associated with each other. The display control unit classifies endoscopic images associated with the respective pieces of findings-diagnosis information by the associating unit, into corresponding groups of the respective pieces of findings-diagnosis information and causes the endoscopic images to be displayed and switched on a group-by-group basis by using tabs.

According to the aspect, endoscopic images associated with respective pieces of findings-diagnosis information are each classified into a corresponding one of groups corresponding to the respective pieces of findings-diagnosis information, and the endoscopic images are displayed and switched on a group-by-group basis by using tabs. This thus allows the endoscopic images to be checked for each of the groups corresponding to the respective pieces of findings-diagnosis information.

The accepting unit preferably accepts an operation, on the input device, of selecting a tab, and the display control unit preferably causes an endoscopic image classified into a group corresponding to the selected tab to be displayed in the image display area. This thus allows the endoscopic image belonging to the group corresponding to the selected tab to be checked.

The display control unit preferably classifies all selectable endoscopic images into a single group. This thus allows all the selectable endoscopic images to be checked.

The accepting unit preferably accepts an operation of dragging and dropping at least one endoscopic image among the endoscopic images displayed in the image display area onto a piece of findings-diagnosis information displayed in the findings-diagnosis information display area, and the associating unit preferably associates the dragged and dropped endoscopic image with the piece of findings-diagnosis information. This thus allows an endoscopic image and a piece of findings-diagnosis information relating to the endoscopic image to be appropriately selected.

The accepting unit preferably accepts an operation of dragging and dropping at least one piece of findings-diagnosis information among the pieces of findings-diagnosis information displayed in the findings-diagnosis information display area onto an endoscopic image displayed in the image display area, and the associating unit preferably associates the dragged and dropped piece of findings-diagnosis information with the endoscopic image onto which the piece of findings-diagnosis information is dropped. This thus allows an endoscopic image and a piece of findings-diagnosis information relating to the endoscopic image to be appropriately selected.

The display control unit preferably causes identification information indicating the piece of findings-diagnosis information associated with the endoscopic image to be displayed along with the endoscopic image in the image display area. This thus allows the piece of findings-diagnosis information associated with each endoscopic image to be checked.

The display control unit preferably causes the identification information to be displayed at the corresponding tab. This thus allows the tab to be appropriately identified.

The identification information is preferably a number corresponding to the piece of findings-diagnosis information. This thus allows the identification information to be appropriately displayed.

The display control unit preferably causes the identification information to be displayed along with the piece of findings-diagnosis information in the findings-diagnosis information display area. This allows a user to recognize a correspondence between the piece of findings-diagnosis information and the number.

The display control unit preferably causes the selected images to be displayed in an overlapping manner. This thus can reduce the number of displayed images and can make it easier to select endoscopic images.

The accepting unit preferably accepts an operation of designating position information of a lesion contained in the endoscopic image, and the recording control unit preferably causes the recording apparatus to record therein the designated position information as the training data. This thus allows the position information of the lesion to be included in the training data.

To accomplish the above object, a training system according to an aspect is a training system including: a display device; an input device; a recording apparatus; a training data collection apparatus including a display control unit that causes one or a plurality of endoscopic images captured with an endoscope to be displayed in an image display area of the display device and that causes one or a plurality of pieces of findings-diagnosis information on a lesion to be displayed in a findings-diagnosis information display area of the display device, an accepting unit that accepts an operation on the input device, the operation being an operation of selecting at least one endoscopic image from among the endoscopic images displayed in the image display area and a piece of findings-diagnosis information relating to the at least one endoscopic image from among the pieces of findings-diagnosis information displayed in the findings-diagnosis information display area, an associating unit that associates the selected endoscopic image with the selected piece of findings-diagnosis information, and a recording control unit that causes the recording apparatus to record therein, as training data for use in training of a model that discriminates a lesion from an endoscopic image, the endoscopic image and the piece of findings-diagnosis information associated with each other, the display control unit being configured to classify endoscopic images associated with the respective pieces of findings-diagnosis information by the associating unit, into corresponding groups of the respective pieces of findings-diagnosis information and to cause the endoscopic images to be displayed and switched on a group-by-group basis by using tabs; and a discriminator that discriminates a lesion from an endoscopic image by using a model. The model is trained using the training data.

According to the aspect, a model can be appropriately trained using training data that is collected by the training data collection apparatus that enables endoscopic images associated with respective pieces of findings-diagnosis information to be checked.

To accomplish the above object, a trained model according to an aspect is a trained model that has been trained by a training system including: a display device; an input device; a recording apparatus; a training data collection apparatus including a display control unit that causes one or a plurality of endoscopic images captured with an endoscope to be displayed in an image display area of the display device and that causes one or a plurality of pieces of findings-diagnosis information on a lesion to be displayed in a findings-diagnosis information display area of the display device, an accepting unit that accepts an operation on the input device, the operation being an operation of selecting at least one endoscopic image from among the endoscopic images displayed in the image display area and a piece of findings-diagnosis information relating to the at least one endoscopic image from among the pieces of findings-diagnosis information displayed in the findings-diagnosis information display area, an associating unit that associates the selected endoscopic image with the selected piece of findings-diagnosis information, and a recording control unit that causes the recording apparatus to record therein, as training data for use in training of a model that discriminates a lesion from an endoscopic image, the endoscopic image and the piece of findings-diagnosis information associated with each other, the display control unit being configured to classify endoscopic images associated with the respective pieces of findings-diagnosis information by the associating unit, into corresponding groups of the respective pieces of findings-diagnosis information and to cause the endoscopic images to be displayed and switched on a group-by-group basis by using tabs; and a discriminator that discriminates a lesion from an endoscopic image by using a model, in which the model is trained using the training data.

According to the aspect, a trained model that has been trained using appropriately collected training data can be obtained.

To accomplish the above object, an endoscopic image processing apparatus according to an aspect is an endoscopic image processing apparatus that analyzes an endoscopic image using a trained model that has been trained by a training system which includes a discriminator that discriminates a lesion from an endoscopic image using a model and which trains the model using training data, the training system including: a display device; an input device; a recording apparatus; and a training data collection apparatus including a display control unit that causes one or a plurality of endoscopic images captured with an endoscope to be displayed in an image display area of the display device and that causes one or a plurality of pieces of findings-diagnosis information on a lesion to be displayed in a findings-diagnosis information display area of the display device, an accepting unit that accepts an operation on the input device, the operation being an operation of selecting at least one endoscopic image from among the endoscopic images displayed in the image display area and a piece of findings-diagnosis information relating to the at least one endoscopic image from among the pieces of findings-diagnosis information displayed in the findings-diagnosis information display area, an associating unit that associates the selected endoscopic image with the selected piece of findings-diagnosis information, and a recording control unit that causes the recording apparatus to record therein, as training data for use in training of a model that discriminates a lesion from an endoscopic image, the endoscopic image and the piece of findings-diagnosis information associated with each other, the display control unit being configured to classify endoscopic images associated with the respective pieces of findings-diagnosis information by the associating unit, into corresponding groups of the respective pieces of findings-diagnosis information and to cause the endoscopic images to be displayed and switched on a group-by-group basis by using tabs, in which the model is trained using the training data.

According to the aspect, an endoscopic image can be analyzed by using a trained model that has been trained using appropriately collected training data.

To accomplish the above object, a training data collection method according to an aspect is a training data collection method including: a display control step of causing one or a plurality of endoscopic images captured with an endoscope to be displayed in an image display area of a display device and causing one or a plurality of pieces of findings-diagnosis information on a lesion to be displayed in a findings-diagnosis information display area of the display device; an accepting step of accepting an operation on an input device, the operation being an operation of selecting at least one endoscopic image from among the endoscopic images displayed in the image display area and a piece of findings-diagnosis information relating to the at least one endoscopic image from among the pieces of findings-diagnosis information displayed in the findings-diagnosis information display area; an association step of associating the selected endoscopic image with the selected piece of findings-diagnosis information; and a recording control step of causing a recording apparatus to record therein, as training data for use in training of a model that discriminates a lesion from an endoscopic image, the endoscopic image and the piece of findings-diagnosis information associated with each other. The display control step classifies endoscopic images associated with the respective pieces of findings-diagnosis information in the association step, into corresponding groups of the respective pieces of findings-diagnosis information and causes the endoscopic images to be displayed and switched on a group-by-group basis by using tabs.

According to the aspect, endoscopic images associated with respective pieces of findings-diagnosis information are each classified into a corresponding one of groups corresponding to the respective pieces of findings-diagnosis information, and the endoscopic images are displayed and switched on a group-by-group basis by using tabs. This thus allows the endoscopic images to be checked for each of the groups corresponding to the respective pieces of findings-diagnosis information.

To accomplish the above object, a program that causes a computer to execute a training data collection method is a program that causes a computer to execute a training data collection method including: a display control step of causing one or a plurality of endoscopic images captured with an endoscope to be displayed in an image display area of a display device and causing one or a plurality of pieces of findings-diagnosis information on a lesion to be displayed in a findings-diagnosis information display area of the display device; an accepting step of accepting an operation on an input device, the operation being an operation of selecting at least one endoscopic image from among the endoscopic images displayed in the image display area and a piece of findings-diagnosis information relating to the at least one endoscopic image from among the pieces of findings-diagnosis information displayed in the findings-diagnosis information display area; an association step of associating the selected endoscopic image with the selected piece of findings-diagnosis information; and a recording control step of causing a recording apparatus to record therein, as training data for use in training of a model that discriminates a lesion from an endoscopic image, the endoscopic image and the piece of findings-diagnosis information associated with each other. The display control step classifies endoscopic images associated with the respective pieces of findings-diagnosis information in the association step, into corresponding groups of the respective pieces of findings-diagnosis information and causes the endoscopic images to be displayed and switched on a group-by-group basis by using tabs.

According to the aspect, endoscopic images associated with respective pieces of findings-diagnosis information are each classified into a corresponding one of groups corresponding to the respective pieces of findings-diagnosis information, and the endoscopic images are displayed and switched on a group-by-group basis by using tabs. This thus allows the endoscopic images to be checked for each of the groups corresponding to the respective pieces of findings-diagnosis information.

According to the aspects, training data for use in training of a model that discriminates a lesion from an endoscopic image can be easily collected.

DESCRIPTION OF THE PREFERRED EMBODIMENTS

Preferred embodiments of the present invention will be described in detail below with reference to the accompanying drawings.

First Embodiment

[Configuration of Endoscopic-Image-Based Training System]

Figure 1:
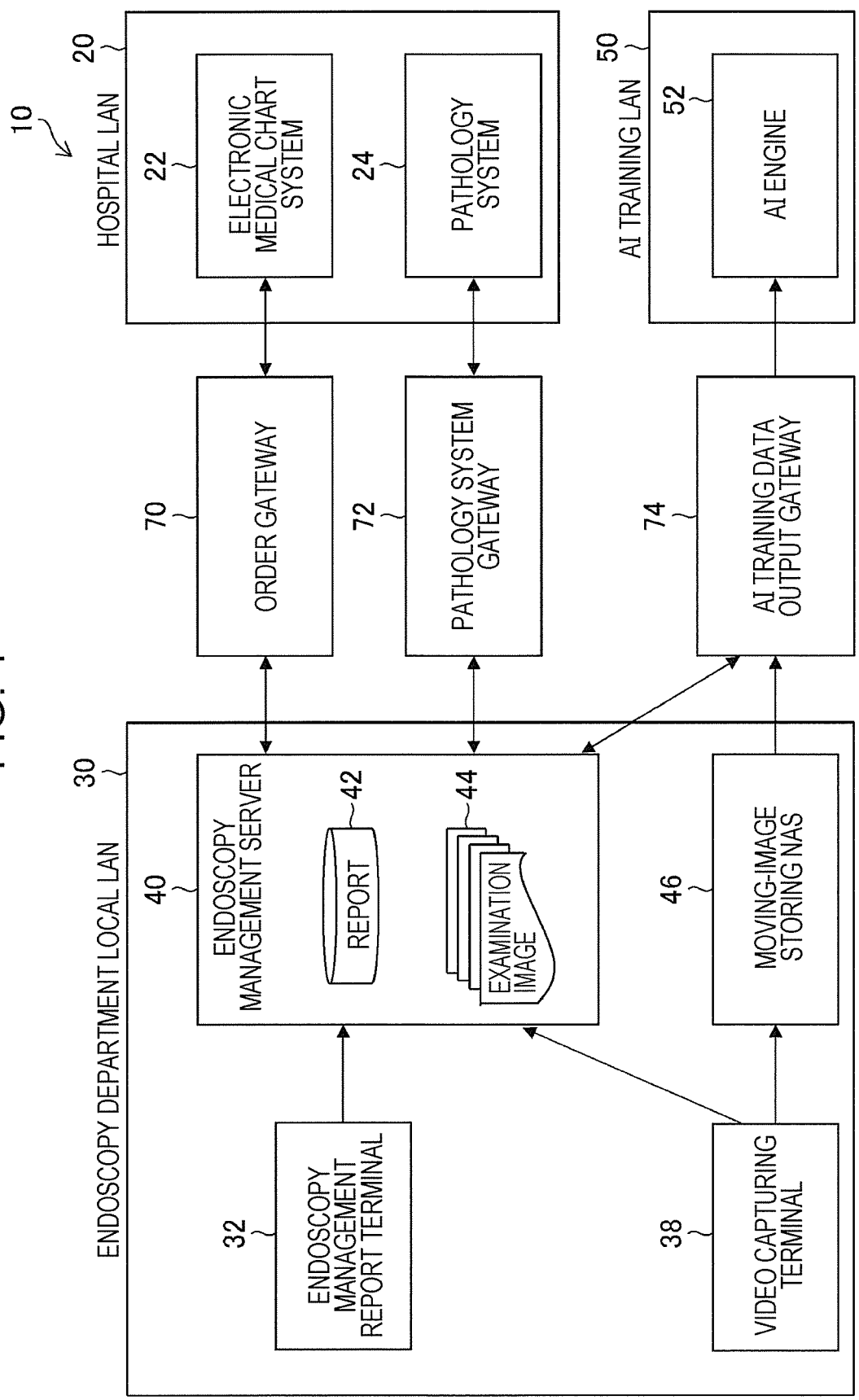
FIG. 1 is a block diagram illustrating an example of a configuration of an endoscopic-image-based training system.

FIG. 1 is a block diagram illustrating an example of a configuration of an endoscopic-image-based training system 10. The endoscopic-image-based training system 10 includes a hospital local area network (LAN) 20 constructed in a hospital, an endoscopy department local LAN 30 constructed in an endoscopy department of the hospital, an artificial intelligence (AI) training LAN 50 constructed in or outside the hospital, and so on.

An electronic medical chart system 22 and a pathology system 24 are connected to the hospital LAN 20.

The electronic medical chart system 22 is a system that manages examination information of all the patients at the hospital. In addition, the pathology system 24 is a system that manages pathological specimens and pathological diagnosis information. The electronic medical chart system 22 and the pathology system 24 may be constituted by a single computer, or may be constituted by a plurality of computers in a distributed manner.

An endoscopy management report terminal 32, a video capturing terminal 38, an endoscopy management server 40, and a moving-image storing network attached storage (NAS) 46 are connected to the endoscopy department local LAN 30.

The endoscopy management report terminal 32 is a terminal used by a doctor to create an endoscopy report 42 (described below) regarding an endoscopic examination performed using an endoscope apparatus (not illustrated).

Figure 2:
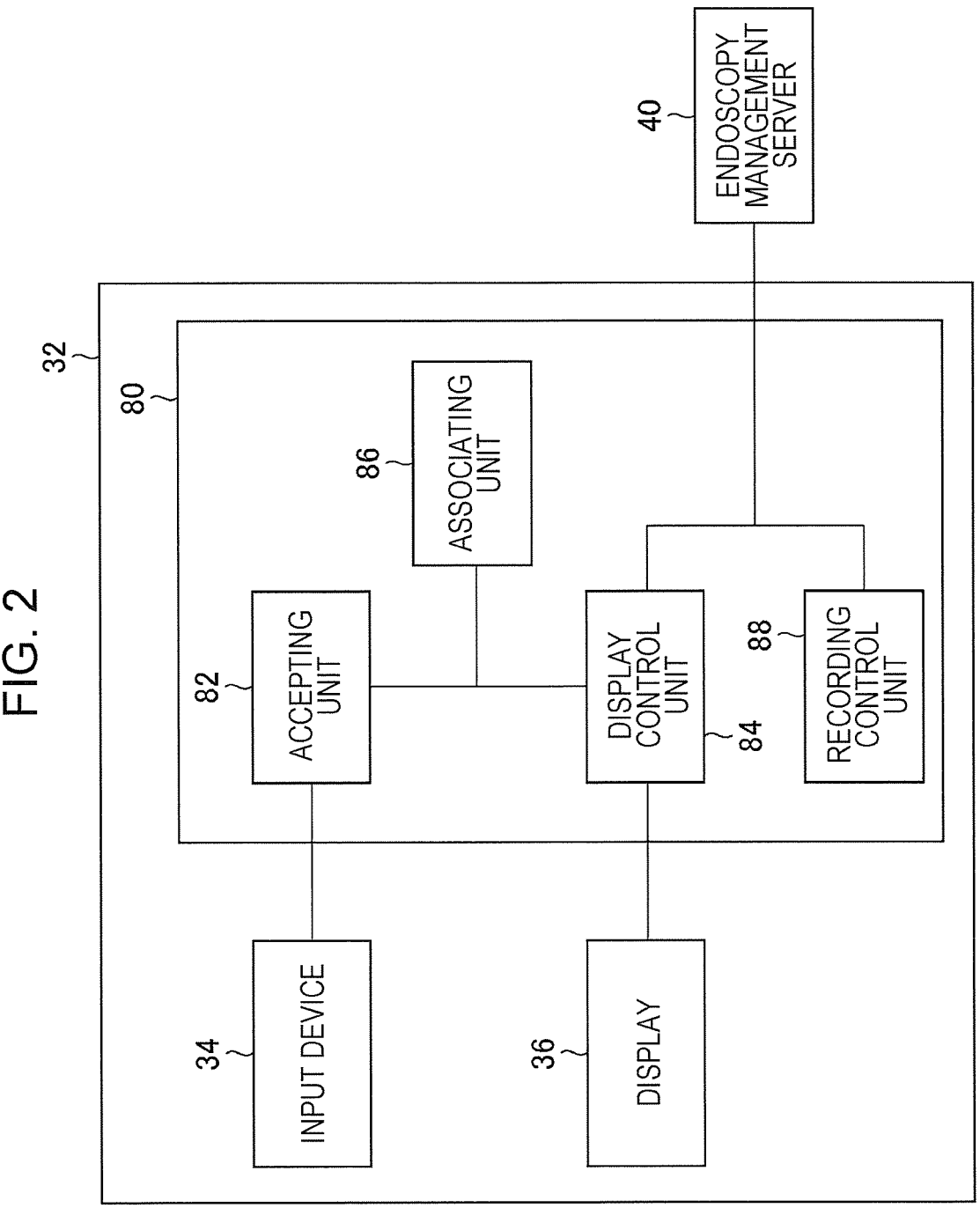
FIG. 2 is a block diagram illustrating an example of a configuration of an endoscopy management report terminal.

FIG. 2 is a block diagram illustrating an example of a configuration of the endoscopy management report terminal 32. The endoscopy management report terminal 32 includes an input device 34, a display 36, and a training data collection apparatus 80.

For example, a mouse or a keyboard is used as the input device 34 (an example of an input device). For example, a liquid crystal monitor is used as the display 36 (an example of a display device). The input device 34 and the display 36 may be integrated together by using a display equipped with a touch panel.

The training data collection apparatus 80 collects training data for use in training of a model that discriminates a lesion from an endoscopic image. The training data collection apparatus 80 includes an accepting unit 82, a display control unit 84, an associating unit 86, and a recording control unit 88.

The accepting unit 82 accepts an operation on the input device 34. The display control unit 84 causes the display 36 to display an endoscopic image and findings-diagnosis information. The associating unit 86 associates an endoscopic image with findings-diagnosis information, based on an associating operation (described below) accepted by the accepting unit 82. The recording control unit 88 causes the endoscopy management server 40 to record therein an endoscopic image and findings-diagnosis information that are associated with each other by the associating unit 86.

Description returns to FIG. 1. The video capturing terminal 38 acquires a moving image captured with a camera of an endoscope apparatus (not illustrated) and transmits the moving image to the moving-image storing NAS 46. The video capturing terminal 38 also acquires a still image captured with the camera of the endoscope apparatus (not illustrated) and transmits the still image to the endoscopy management server 40.

The endoscopy management server 40 manages an endoscope apparatus (not illustrated) via the endoscopy management report terminal 32. The endoscopy management server 40 also records therein the endoscopy report 42 created by the endoscopy management report terminal 32, and an examination image 44 which is a still image captured with a camera of an endoscope apparatus.

The moving-image storing NAS 46 records therein a moving image captured with a camera of an endoscope apparatus.

An AI engine 52 is connected to the AI training LAN 50. The AI engine 52 discriminates a lesion contained in an endoscopic image input thereto, and outputs information on the discriminated lesion. The AI engine 52 is constituted by, for example, a graphics processing unit (GPU).

Figure 3:
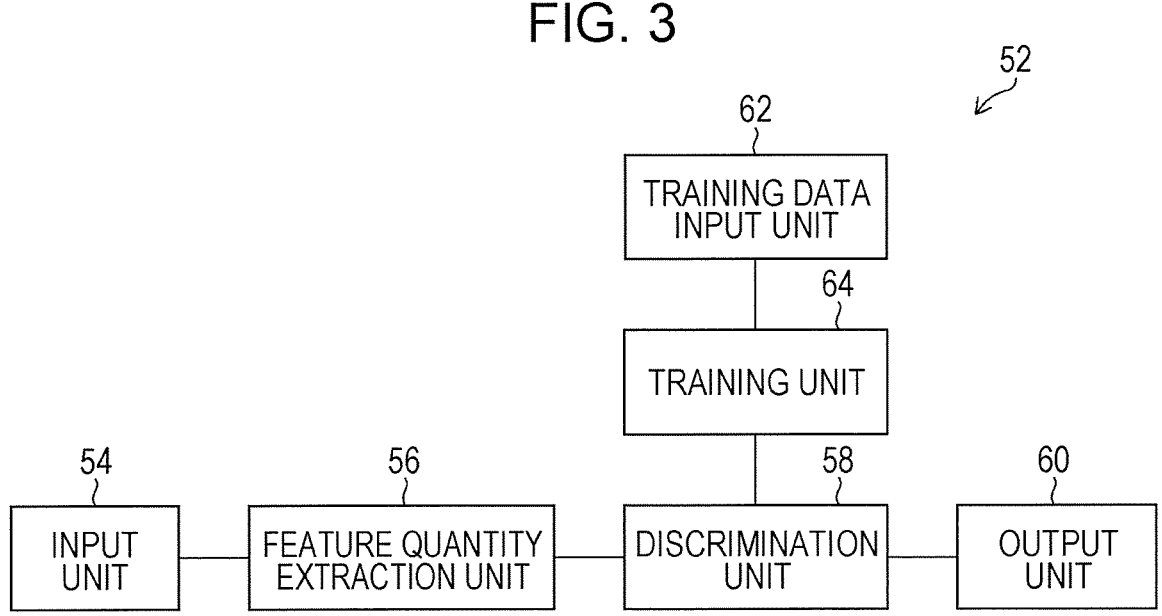
FIG. 3 is a block diagram illustrating an example of a configuration of an AI engine.

FIG. 3 is a block diagram illustrating an example of a configuration of the AI engine 52. The AI engine 52 includes an input unit 54, a feature quantity extraction unit 56, a discrimination unit 58, an output unit 60, a training data input unit 62, and a training unit 64.

An endoscopic image is input to the input unit 54. An endoscopic image is not limited to a still image and may be a moving image.

The feature quantity extraction unit 56 extracts a feature quantity from an endoscopic image input to the input unit 54. The discrimination unit 58 (an example of a discriminator) discriminates a lesion contained in the endoscopic image by using a model, based on the feature quantity extracted by the feature quantity extraction unit 56. The output unit 60 outputs information on the lesion discriminated by the discrimination unit 58.

Training data for use in training of a model is input to the training data input unit 62. The training unit 64 includes a model similar to that of the discrimination unit 58. The training unit 64 trains the model using the training data input to the training data input unit 62. The trained model that has been trained by the training unit 64 is input to the discrimination unit 58. Thus, the model of the discrimination unit 58 is updated to the trained model.

The feature quantity extraction unit 56 and the discrimination unit 58 may be configured to discriminate a lesion contained in an endoscopic image by using the model, and the training unit 64 may train the model of the feature quantity extraction unit 56 and the discrimination unit 58 to update the model to the trained model.

Description again returns to FIG. 1. The electronic medical chart system 22 and the endoscopy management server 40 are connected to each other via an order gateway 70. The order gateway 70 is constituted by a single computer server. The order gateway 70 receives examination information and patient information from the electronic medical chart system 22 or an ordering system (not illustrated), and transmits examination order information to the endoscopy management server 40. The endoscopy management server 40 records therein the received examination order information.

The order gateway 70 also receives the endoscopy report 42 and examination record information from the endoscopy management server 40, and transmits the endoscopy report 42 and the examination record information to the electronic medical chart system 22 or a medical accounting system (not illustrated).

The pathology system 24 and the endoscopy management server 40 are connected to each other via a pathology system gateway 72. The pathology system gateway 72 is constituted by a single computer server. The pathology system gateway 72 acquires a pathological diagnosis result from the pathology system 24, and transmits the pathological diagnosis result to the endoscopy management server 40. The endoscopy management server 40 records therein the received pathological diagnosis result.

The AI engine 52 and the endoscopy management server 40 are connected to each other via an AI training data output gateway 74. The AI training data output gateway 74 receives training data from the endoscopy management server 40, and transmits the training data to the AI engine 52.

[Training Method]

Figure 4:
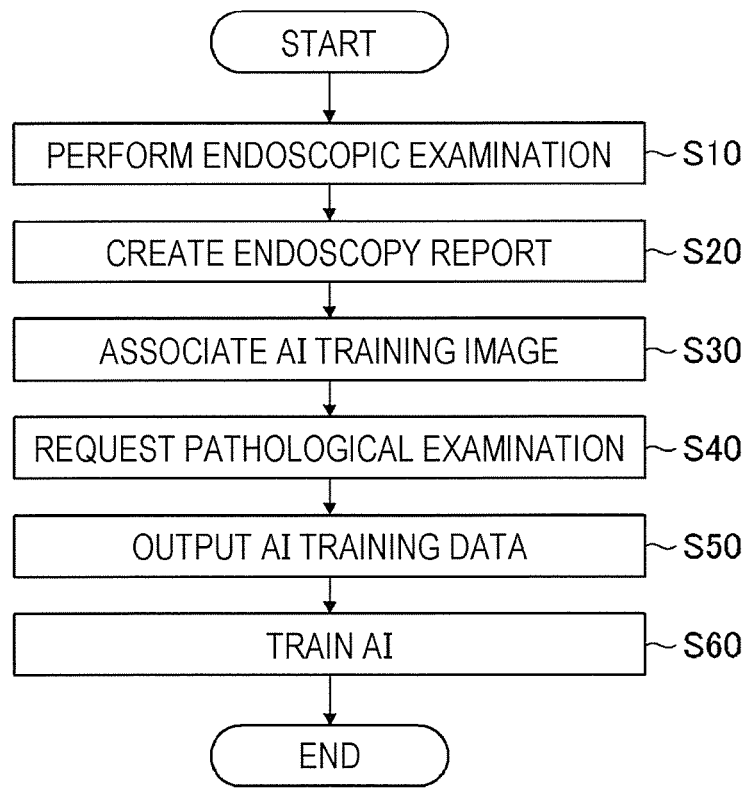
FIG. 4 is a flowchart illustrating a process of a training method.

The endoscopic-image-based training system 10 uses, as training data, endoscopic images and findings-diagnosis information to train a model that discriminates a lesion from an endoscopic image. FIG. 4 is a flowchart illustrating a process of a training method performed using the endoscopic-image-based training system 10. The training method includes an endoscopic examination performing step (step S10), an endoscopy report creation step (step S20), an AI training image association step (step S30), a pathological examination requesting step (step S40), an AI training data output step (step S50), and an AI training step (step S60).

[Details of Endoscopic Examination Performing Step]

Figure 5:
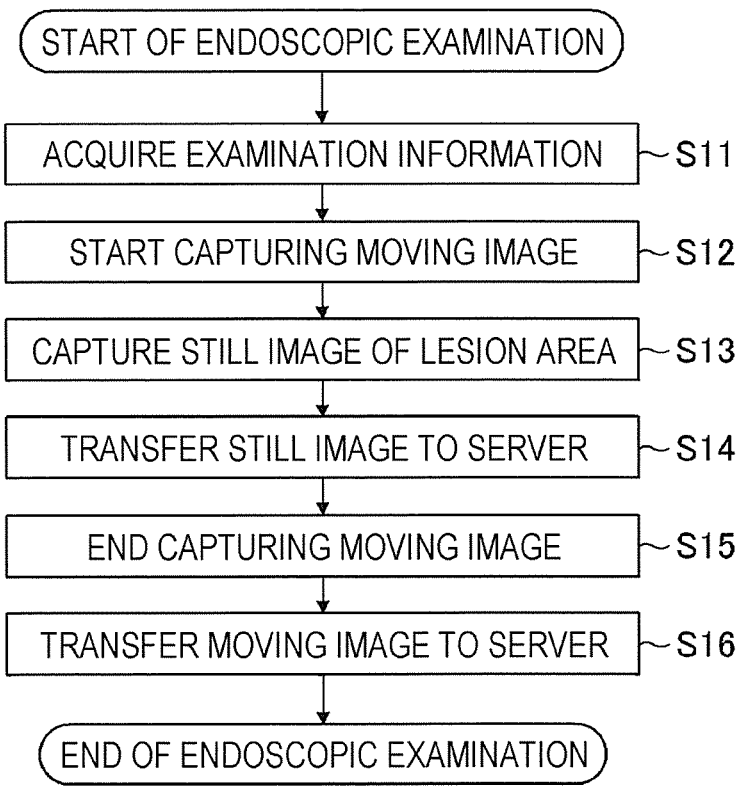
FIG. 5 is a flowchart illustrating detailed processing of an endoscopic examination performing step.

In the endoscopic examination performing step, an endoscopic examination is performed on a patient. FIG. 5 is a flowchart illustrating detailed processing of the endoscopic examination performing step. The endoscopic examination performing step includes an examination information acquisition step (step S11), a moving-image capturing start step (step S12), a lesion-area still-image capturing step (step S13), a still-image server transfer step (step S14), a moving-image capturing end step (step S15), and a moving-image server transfer step (step S16).

<Examination Information Acquisition Step (Step S11)>

In the examination information acquisition step, examination information on an endoscopic examination to be performed is acquired. A doctor inputs the examination information using the input device 34 of the endoscopy management report terminal 32. The examination information includes information such as to-be-examined-area information, the examination date, and the name, age, and gender of the patient. The input examination information is transmitted from the endoscopy management report terminal 32 to the endoscopy management server 40.

<Moving-Image Capturing Start Step (Step S12)>

In the moving-image capturing start step, capturing of an endoscopic moving image is started. The doctor operates a camera of an endoscope apparatus (not illustrated) to capture a moving image. The captured moving image is displayed in real time on a display device of the endoscope apparatus (not illustrated). In addition, the captured moving image is input to the video capturing terminal 38 at any time.

<Lesion-Area Still-Image Capturing Step (Step S13)>

In the lesion-area still-image capturing step, an endoscopic still image of a lesion area is captured. The doctor observes the captured moving image on the display device of the endoscope apparatus, and operates the camera of the endoscope apparatus (not illustrated) when a lesion area is in the moving image to capture a still image.

<Still-Image Server Transfer Step (Step S14)>

In the still-image server transfer step, the captured still image is transferred to the endoscopy management server 40. The still image captured in the lesion-area still-image capturing step is transmitted from the camera of the endoscope apparatus (not illustrated) to the video capturing terminal 38. The video capturing terminal 38 transmits the received still image to the endoscopy management server 40. The endoscopy management server 40 records therein the received still image as the examination image 44. The endoscopy management server 40 may record therein, along with the examination image 44, a thumbnail image which is a reduced-size examination image.

<Moving-Image Capturing End Step (Step S15)>

In the moving-image capturing end step, capturing of the moving image is ended. The doctor ends capturing of the moving image using the camera of the endoscope apparatus (not illustrated) when ending the endoscopic examination.

<Moving-Image Server Transfer Step (Step S16)>

In the moving-image server transfer step, the captured moving image is transferred to the moving-image storing NAS 46. The captured moving image is transferred to the video capturing terminal 38 at any time. In the moving-image server transfer step, the moving image is transferred from the video capturing terminal 38 to the moving-image storing NAS 46. The moving-image storing NAS 46 records therein, as an examination image, the moving image transferred thereto.

The endoscopic examination performing step then ends.

[Details of Endoscopy Report Creation Step]

In the endoscopy report creation step, the endoscopy report 42 regarding the endoscopic examination that has been performed in the endoscopic examination performing step is created. The endoscopy report 42 is created by the doctor using the endoscopy management report terminal 32.

Figure 6:
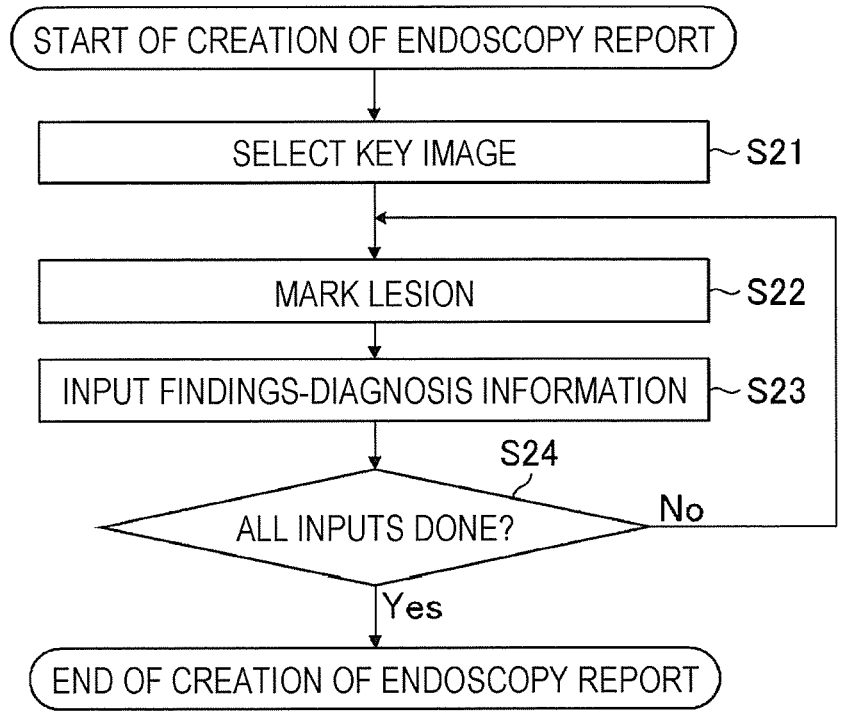
FIG. 6 is a flowchart illustrating detailed processing of an endoscopy report creation step.

FIG. 6 is a flowchart illustrating detailed processing of the endoscopy report creation step. The endoscopy report creation step includes a key image selection step (step S21), a lesion marking step (step S22), a findings-diagnosis information input step (step S23), and an end determination step (step S24).

<Key Image Selection Step (Step S21)>

In the key image selection step, the doctor selects a key image to be used in creation of the endoscopy report 42. A key image is, for example, an image clearly containing a lesion. The display control unit 84 causes the display 36 to display examination images recorded in the endoscopy management server 40. The doctor selects a key image from among the displayed examination images using the input device 34. The number of key images is not limited.

<Lesion Marking Step (Step S22)>

In the lesion marking step, a lesion marking indicating the position of the lesion is added to the key image. The doctor adds the lesion marking to the key image displayed on the display 36 using the input device 34.

<Findings-Diagnosis Information Input Step (Step S23)>

In the findings-diagnosis information input step, findings-diagnosis information constituted by findings information and diagnosis information is input. The doctor inputs the findings-diagnosis information regarding the endoscopic examination and the key image using the input device 34.

<End Determination Step (Step S24)>

In the end determination step, it is determined whether or not all the inputs have been finished for the selected key image. If the inputs have not been finished, the process returns to step S22 and the similar processing is performed. If all the inputs have been finished, the doctor performs an input indicating so using the input device 34 to complete the endoscopy report 42. The endoscopy report creation step then ends.

[Details of AI Training Image Association Step]

In the AI training image association step, endoscopic images and corresponding pieces of findings-diagnosis information are associated with each other to create training data for use in training of the AI engine 52 (an example of a training data collection method). The AI training image association step is performed using the endoscopy management report terminal 32.

Figure 7:
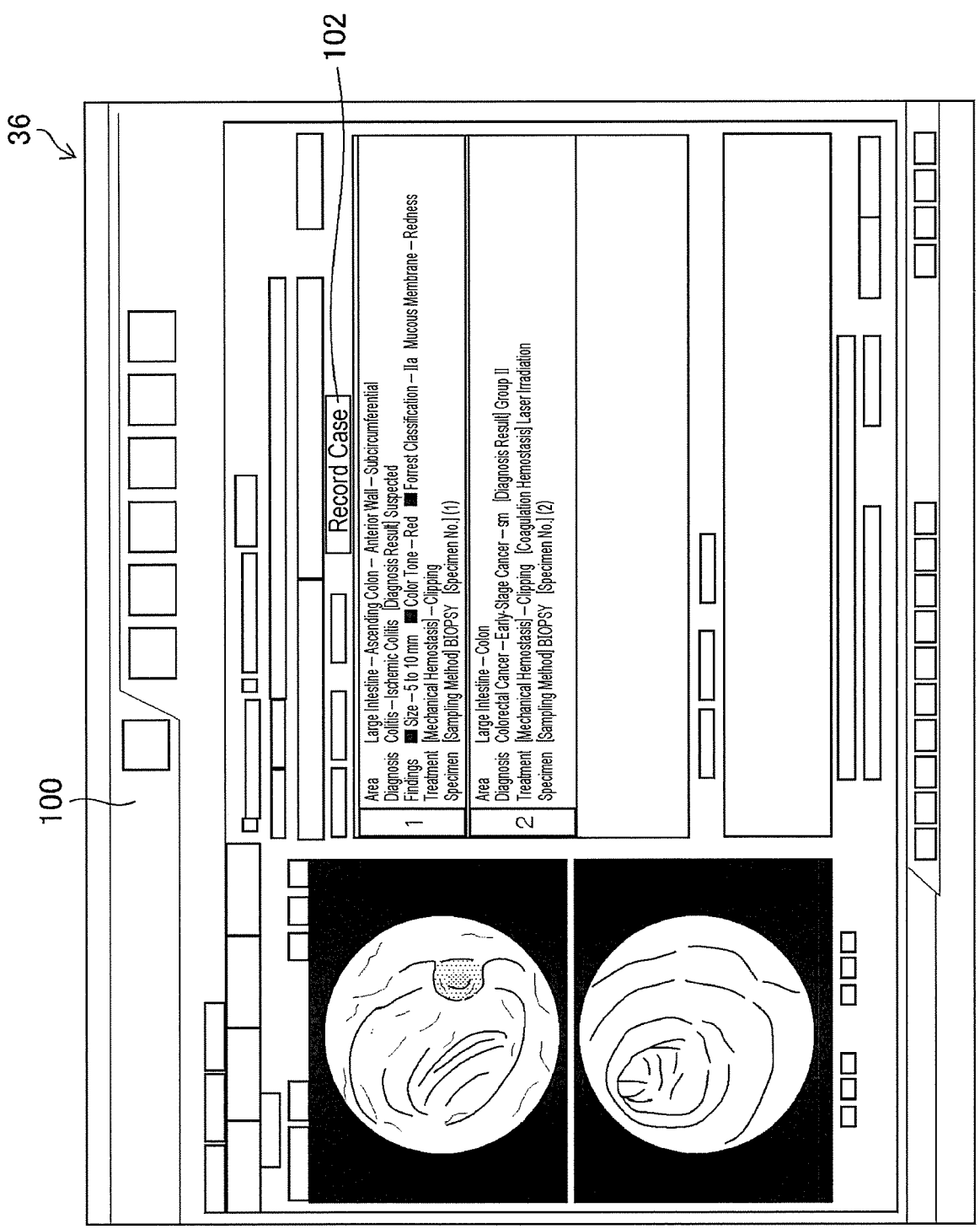
FIG. 7 is a diagram illustrating an example of an endoscopy report creation screen.

FIG. 7 is a diagram illustrating an example of an endoscopy report creation screen 100 displayed on the display 36. The endoscopy report creation step (step S20) described above is performed on the endoscopy report creation screen 100.

A record case button 102 is displayed in the endoscopy report creation screen 100. After creating the endoscopy report 42, the doctor places a pointer at the record case button 102 and clicks at the record case button 102 using a pointing device such as a mouse of the input device 34. This operation causes the screen displayed on the display 36 to shift to an AI training image association screen 110. This operation may be regarded as an input for ending the end determination step (step S24).

Figure 8:
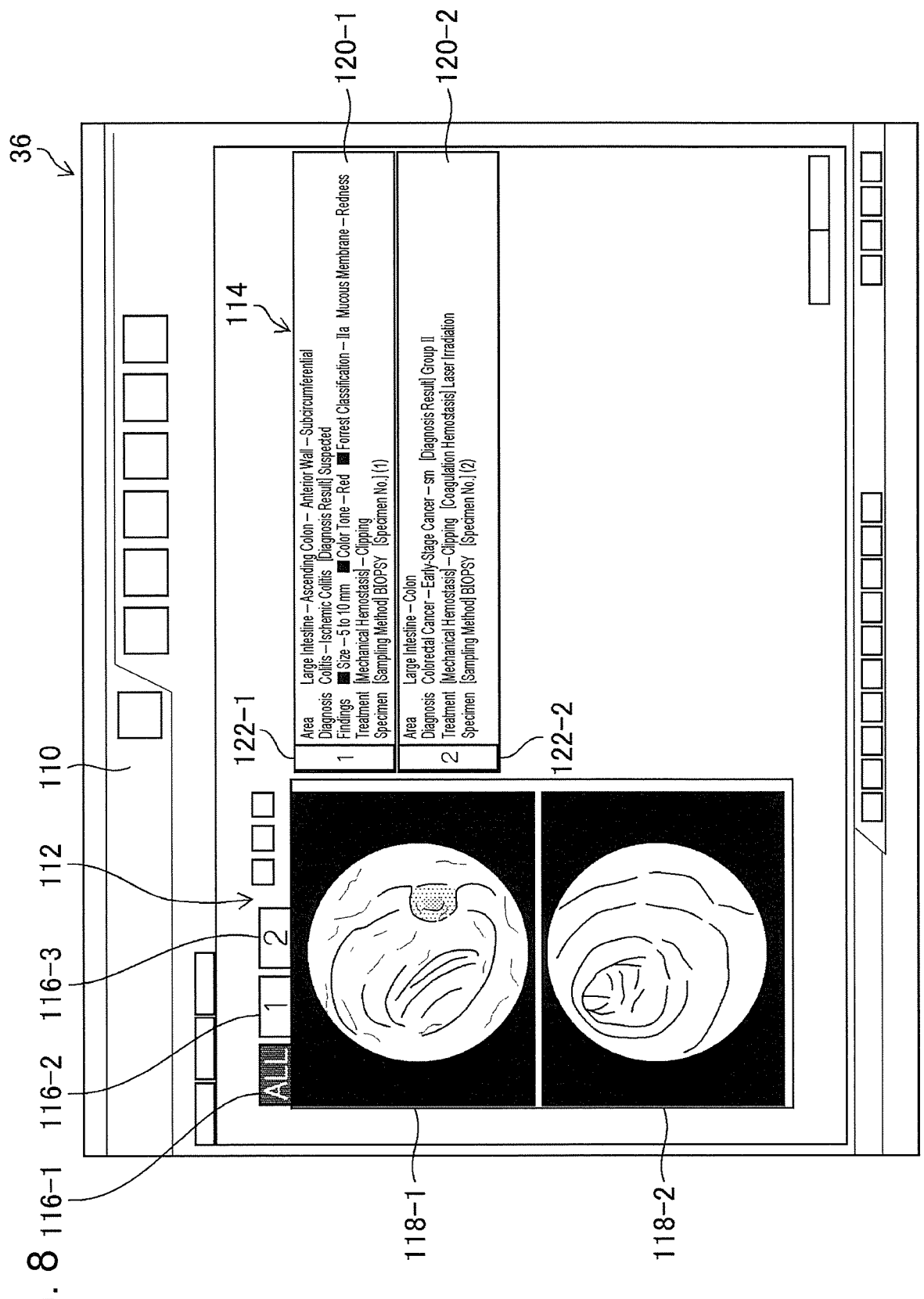
FIG. 8 is a diagram illustrating an example of an AI training image association screen.

FIG. 8 is a diagram illustrating an example of the AI training image association screen 110 displayed on the display 36. The AI training image association step is performed on the AI training image association screen 110. As illustrated in FIG. 8, the AI training image association screen 110 includes an image display area 112 and a findings-diagnosis information display area 114.

The display control unit 84 causes the display 36 to display the AI training image association screen 110. In addition, the display control unit 84 reads out, from the endoscopy management server 40, the examination image(s) 44 of the patient for whom the endoscopy report 42 has been created in the endoscopy report creation step, and causes the examination image(s) to be displayed in the image display area 112 (an example of a display control step).

The display control unit 84 causes a plurality of tabs, any one of which is set active, in the image display area 112. In the example illustrated in FIG. 8, tabs 116-1, 116-2, and 116-3 are displayed.

The display control unit 84 classifies all the examination images that can be associated into a single group, and causes the examination images of this group to be displayed in an area relating to the tab 116-1. If the examination images are still images, thumbnail images of the still images may be displayed. If the examination images are moving images, representative images such as top images of the moving images may be displayed. In the example illustrated in FIG. 8, the tab 116-1 is set active and examination images that can be associated are displayed in the image display area 112. Text "ALL" is displayed for the tab 116-1 to distinguish between kinds of the tabs.

Note that the size of the images displayed in the image display area 112 is appropriately selectable. In the example illustrated in FIG. 8, two examination images 118-1 and 118-2 are displayed in the image display area 112. The number of displayed images can be relatively increased by setting the size of the displayed images relatively small.

The display control unit 84 also reads out, from the endoscopy management server 40, findings-diagnosis information of the patient for whom the endoscopy report 42 has been created in the endoscopy report creation step, and causes the findings-diagnosis information to be displayed in the findings-diagnosis information display area 114 (an example of the display control step). In the example illustrated in FIG. 8, two pieces of findings-diagnosis information 120-1 and 120-2 are displayed. The findings-diagnosis information 120-1 is assigned a number "1" which indicates identification information 122-1 corresponding to the findings-diagnosis information 120-1, and the findings-diagnosis information 120-2 is assigned a number "2" corresponding to identification information 122-2.

The tabs 116-2 and 116-3 displayed in the image display area 112 are tabs relating to the findings-diagnosis information 120-1 and the findings-diagnosis information 120-2, respectively. The number "1" indicating the identification information 122-1 and the number "2" indicating the identification information 122-2 for distinguishing between the kinds of the tabs are displayed for the tabs 116-2 and 116-3, respectively.

Figure 9:
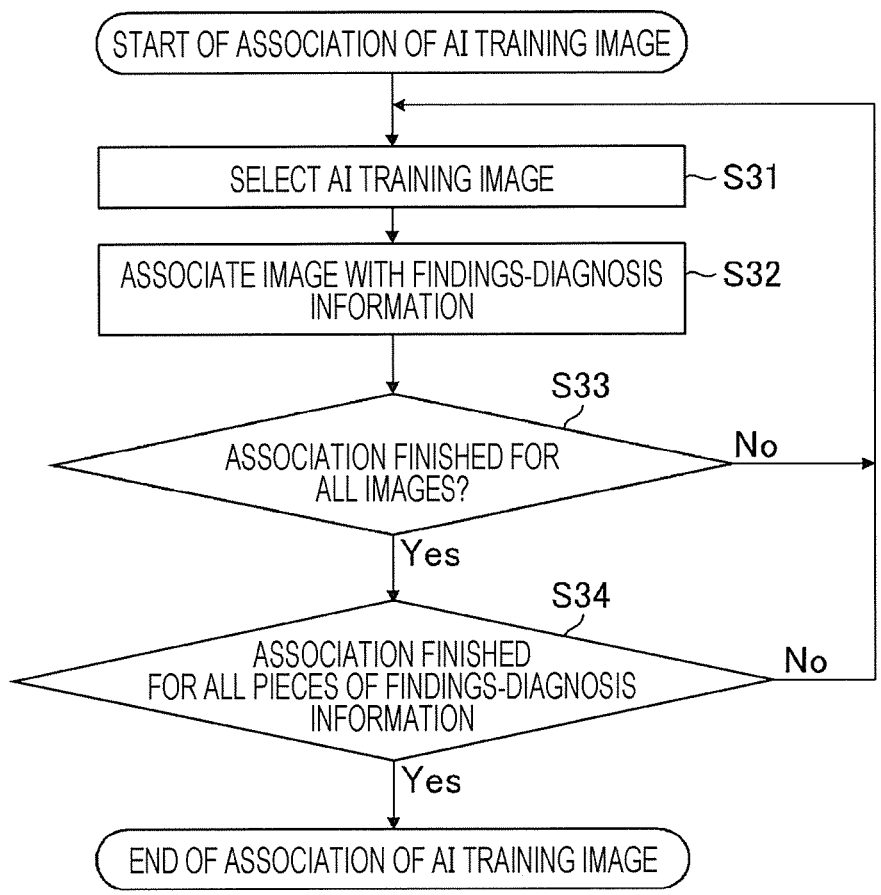
FIG. 9 is a flowchart illustrating detailed processing of the AI training image association step.

FIG. 9 is a flowchart illustrating detailed processing of the AI training image association step. The AI training image association step includes an AI training image selection step (step S31), an association step (step S32), an all image determination step (step S33), and all findings-diagnosis information determination step (step S34).

<AI Training Image Selection Step (Step S31)>

In the AI training image selection step, an examination image for use in training of the AI and findings-diagnosis information on the examination image are selected.

The doctor selects at least one examination image from among the examination images displayed in the image display area 112 of the AI training image association screen 110. The doctor also selects findings-diagnosis information to be associated with the selected examination image from among the pieces of findings-diagnosis information displayed in the findings-diagnosis information display area 114 (an example of an accepting step). The doctor then performs a drag-and-drop operation on the selected examination image onto the position of the selected findings-diagnosis information by using the input device 34.

When a mouse is used, a drag operation is an operation of clicking the left button of the mouse in a state in which the position of the mouse pointer is aligned at the position of the selected examination image and of moving the mouse pointer while maintaining the click operation. During the drag operation, the selected examination image is copied and the copy moves along with movement of the mouse pointer. In addition, a drop operation is an operation of releasing the left button of the mouse in a state in which the mouse pointer subjected to the drag operation or the position of the copy of the examination image is aligned at the selected findings-diagnosis information.

Figure 10:
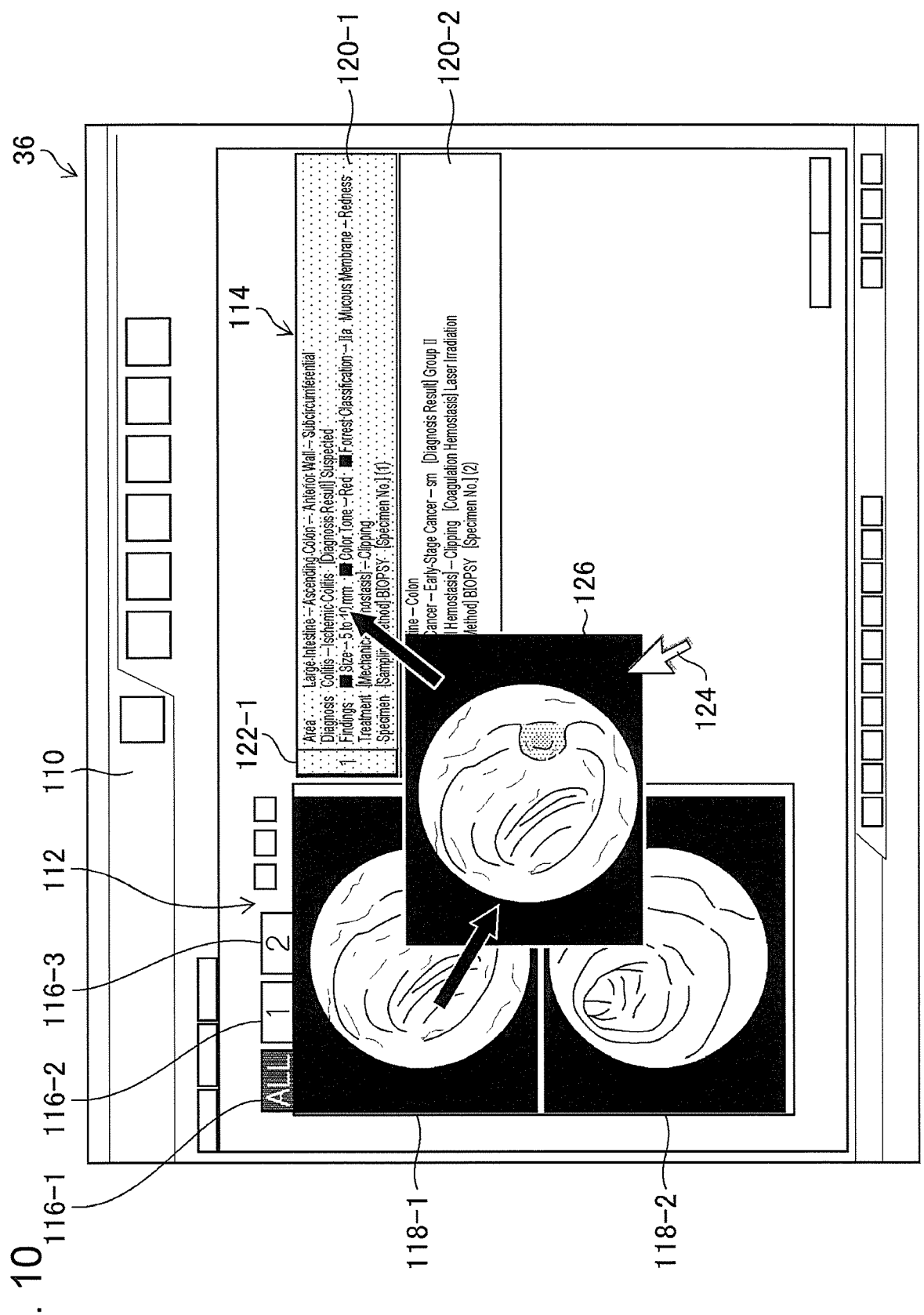
FIG. 10 is a diagram illustrating an example of the AI training image association screen.

FIG. 10 is a diagram illustrating an example of a state in which the drag operation is performed on the selected examination image 118-1 onto the selected findings-diagnosis information 120-1 in the AI training image association screen 110. During the drag operation, a copied image 126 of the selected examination image 118-1 moves along with a mouse pointer 124.

<Association Step (Step S32)>

In the association step, the selected examination image and the selected findings-diagnosis information are associated with each other. In this case, the associating unit 86 associates the examination image that has been dragged and dropped in the AI training image selection step, with the findings-diagnosis information. In the example illustrated in FIG. 10, the examination image 118-1 and the findings-diagnosis information 120-1 are associated with each other.

By dragging and dropping an examination image onto corresponding findings-diagnosis information in this manner, the examination image and the findings-diagnosis information can be easily associated with each other.

Figure 11:
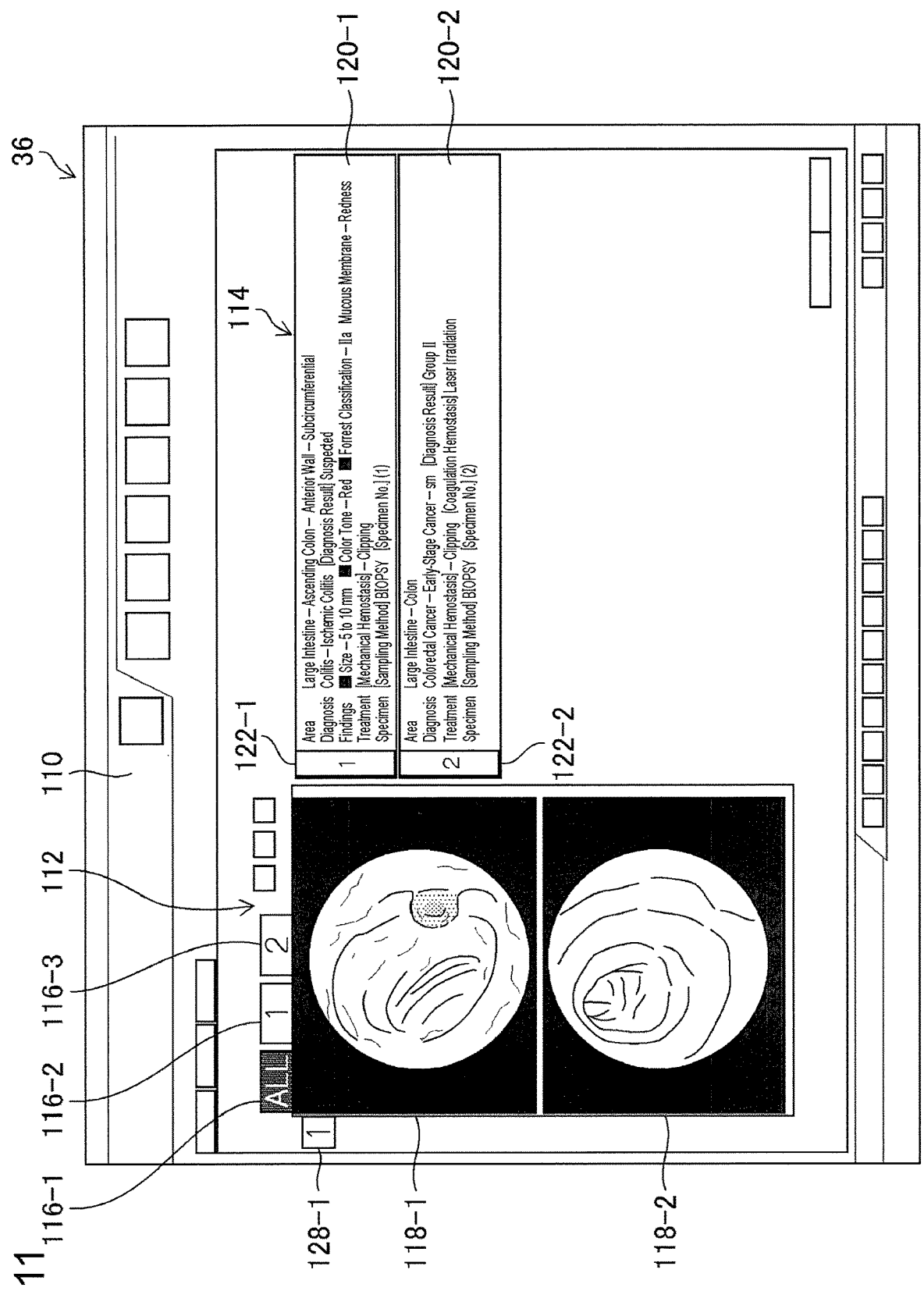
FIG. 11 is a diagram illustrating an example of the AI training image association screen.

FIG. 11 is a diagram illustrating an example of the AI training image association screen 110 after the examination image 118-1 and the findings-diagnosis information 120-1 are associated with each other. The display control unit 84 causes the number "1" of the identification information 122-1 indicating the findings-diagnosis information 120-1 associated with the examination image 118-1 to be displayed, as additional information 128-1, along with the examination image 118-1. This allows the doctor to confirm that the examination image 118-1 and the findings-diagnosis information 120-1 are associated with each other.

Figure 12:
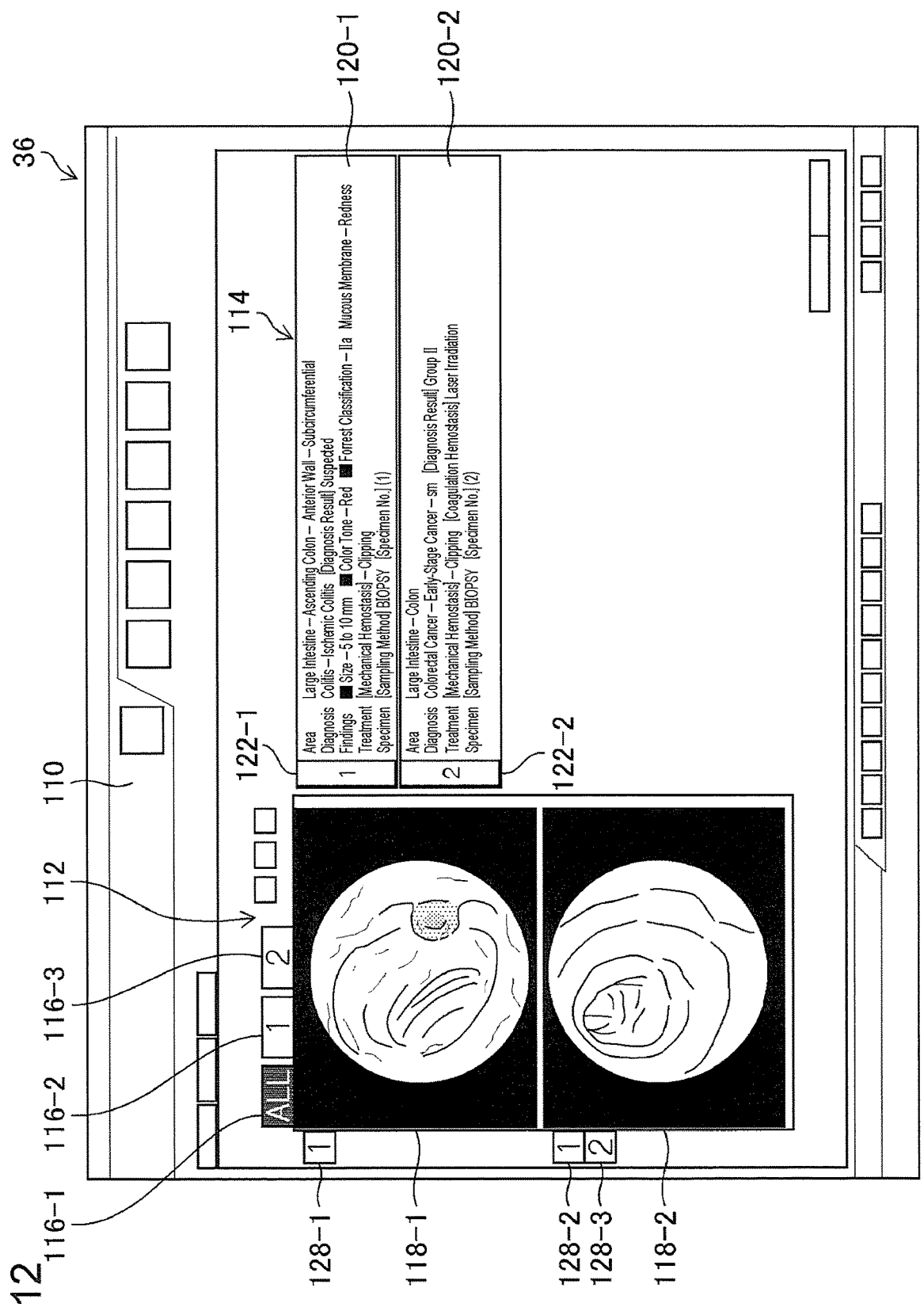
FIG. 12 is a diagram illustrating an example of the AI training image association screen.

FIG. 12 is a diagram illustrating an example of the AI training image association screen 110 after the examination image 118-2 is associated with the findings-diagnosis information 120-1 and the examination image 118-2 is further associated with the findings-diagnosis information 120-2.

Additional information 128-2 indicating the number "1" of the identification information 122-1 and additional information 128-3 indicating the number "2" of the identification information 122-2 are displayed along with the examination image 118-2. This allows the doctor to confine that the examination image 118-2 and the pieces of findings-diagnosis information 120-1 and 120-2 are associated with each other.

Displaying of the additional information indicating the identification information of the findings-diagnosis information along with the associated image in this manner makes findings-diagnosis information that is associated with the image identifiable. In addition, when a single examination image is associated with a plurality of pieces of findings-diagnosis information, the identification information for each of the pieces of the findings-diagnosis information is displayed. This thus makes all the associated pieces of findings-diagnosis information identifiable.

The tab 116-1 is set active in the AI training image association screen 110 illustrated in FIGS. 9 to 12. Alternatively, the doctor can set the tab 116-2 or the tab 116-3 active using the input device 34.

Figure 13:
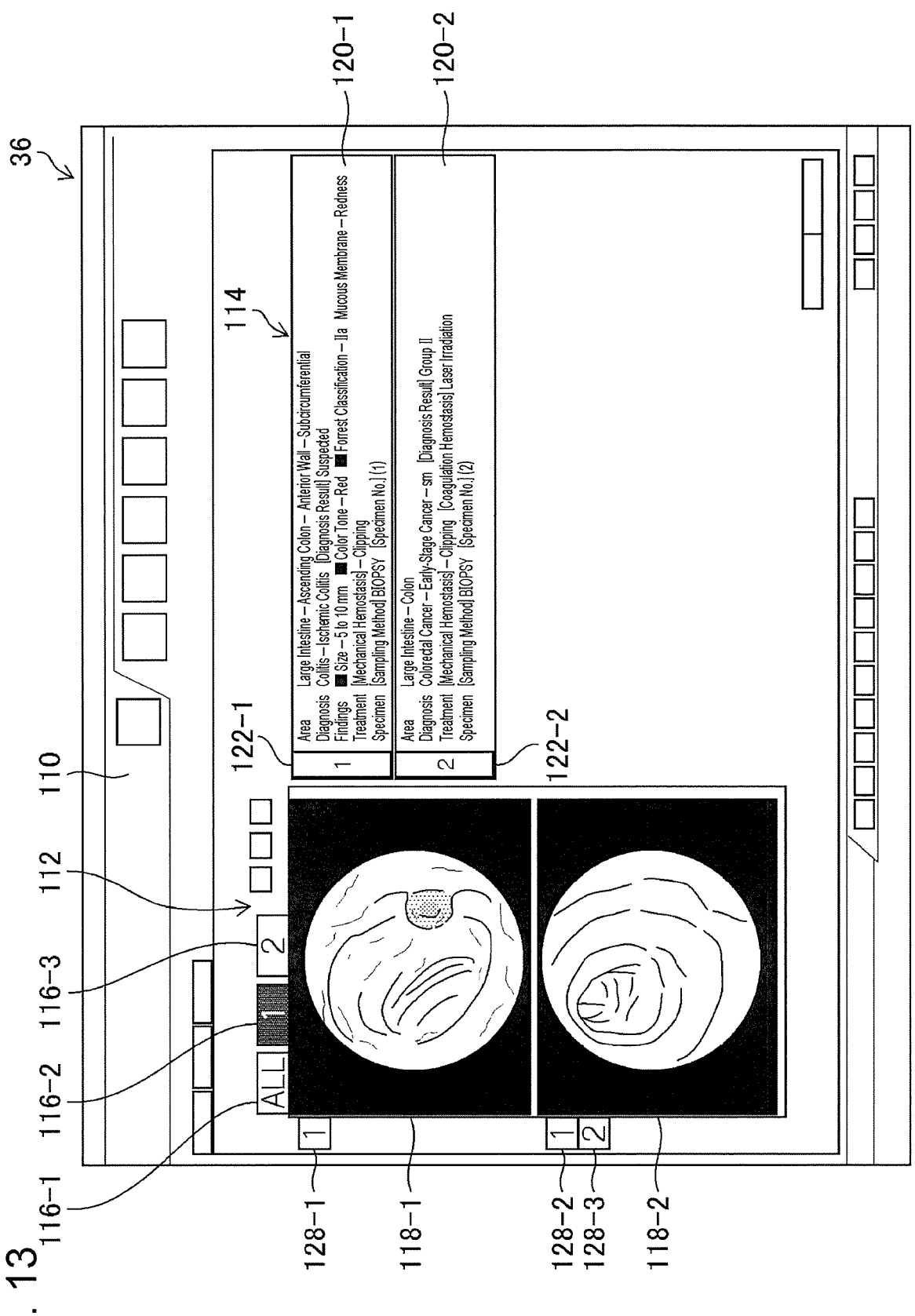
FIG. 13 is a diagram illustrating an example of the AI training image association screen.

FIG. 13 is a diagram illustrating an example of the AI training image association screen 110 in the case where the tab 116-2 is set active in response to the doctor selecting the tab 116-2 in the AI training image association screen 110 illustrated in FIG. 12 using the input device 34. The tab 116-2 is a tab relating to the findings-diagnosis information 120-1. The display control unit 84 classifies examination images associated with the findings-diagnosis information 120-1 into a single group, and causes the examination images of this group to be displayed in an area relating to the tab 116-2. Thus, when the tab 116-2 is selected, the display control unit 84 causes the examination images associated with the findings-diagnosis information 120-1 to be displayed in the image display area 112. In the example illustrated in FIG. 13, the examination images 118-1 and 118-2 associated with the findings-diagnosis information 120-1 are displayed.

Figure 14:
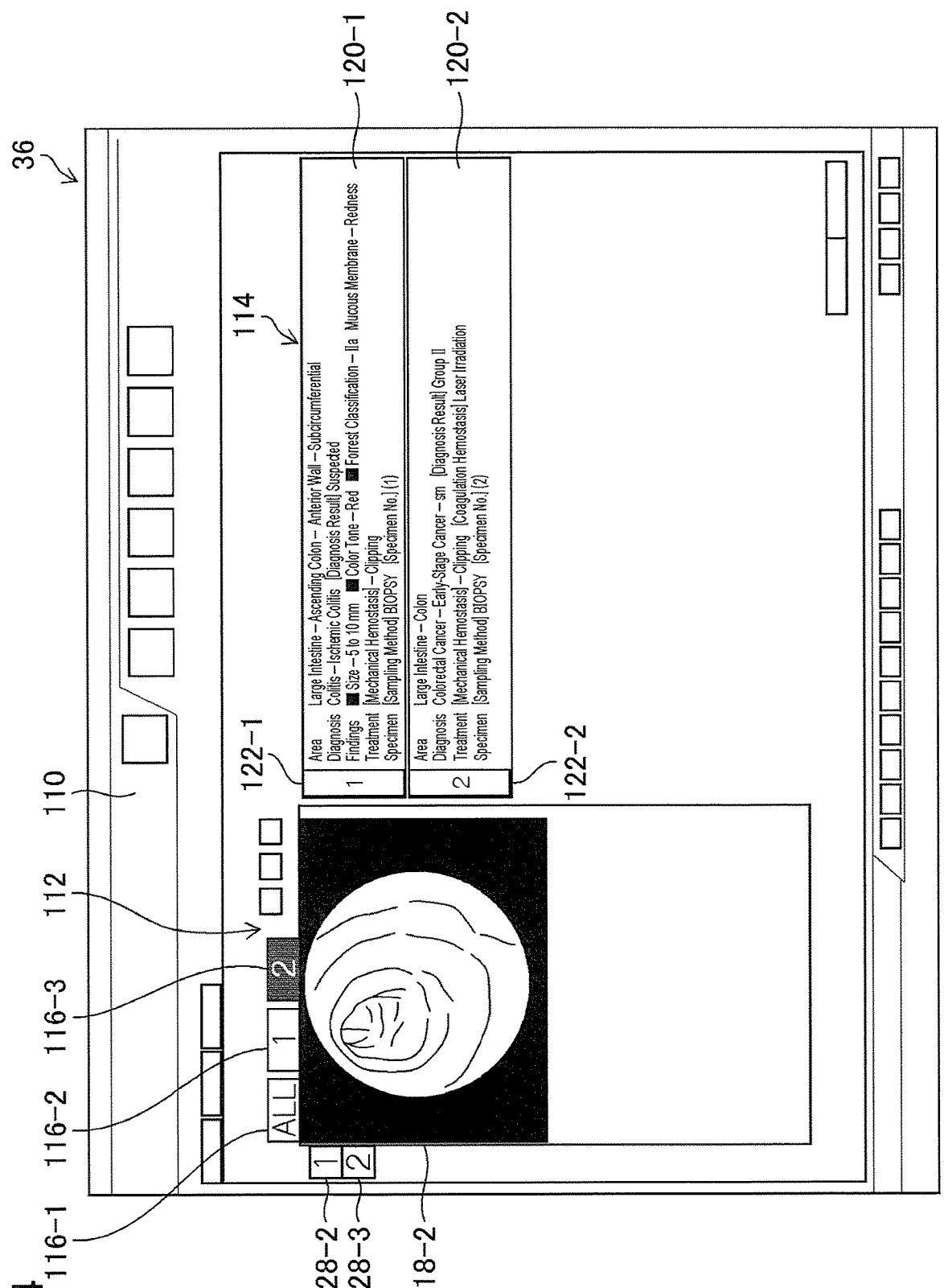
FIG. 14 is a diagram illustrating an example of the AI training image association screen.

In addition, FIG. 14 is a diagram illustrating an example of the AI training image association screen 110 in the case where the tab 116-3 is set active in response to the doctor selecting the tab 116-3 in the AI training image association screen 110 illustrated in FIG. 12 using the input device 34. The tab 116-3 is a tab relating to the findings-diagnosis information 120-2. The display control unit 84 classifies examination images associated with the findings-diagnosis information 120-2 into a single group, and causes the examination images of this group to be displayed in an area relating to the tab 116-3. Thus, when the tab 116-3 is selected, the display control unit 84 causes the examination images associated with the findings-diagnosis information 120-2 to be displayed in the image display area 112. In the example illustrated in FIG. 14, the examination image 118-2 associated with the findings-diagnosis information 120-2 is displayed.

As described above, the display control unit 84 classifies examination images associated with each findings-diagnosis information into a group of the findings-diagnosis information, and causes the examination images to be displayed and switched on a group-by-group basis by using the tabs. Thus, by selecting a desired tab from among a plurality of tabs displayed in the image display area 112, only examination images associated with the findings-diagnosis information relating to the selected tab can be displayed. This allows the doctor to check omission of an image associated with findings-diagnosis information. The doctor checks that there are images necessary for each piece of findings-diagnosis information, and, if there is excess or deficiency, performs the selection operation again.

Figure 15:
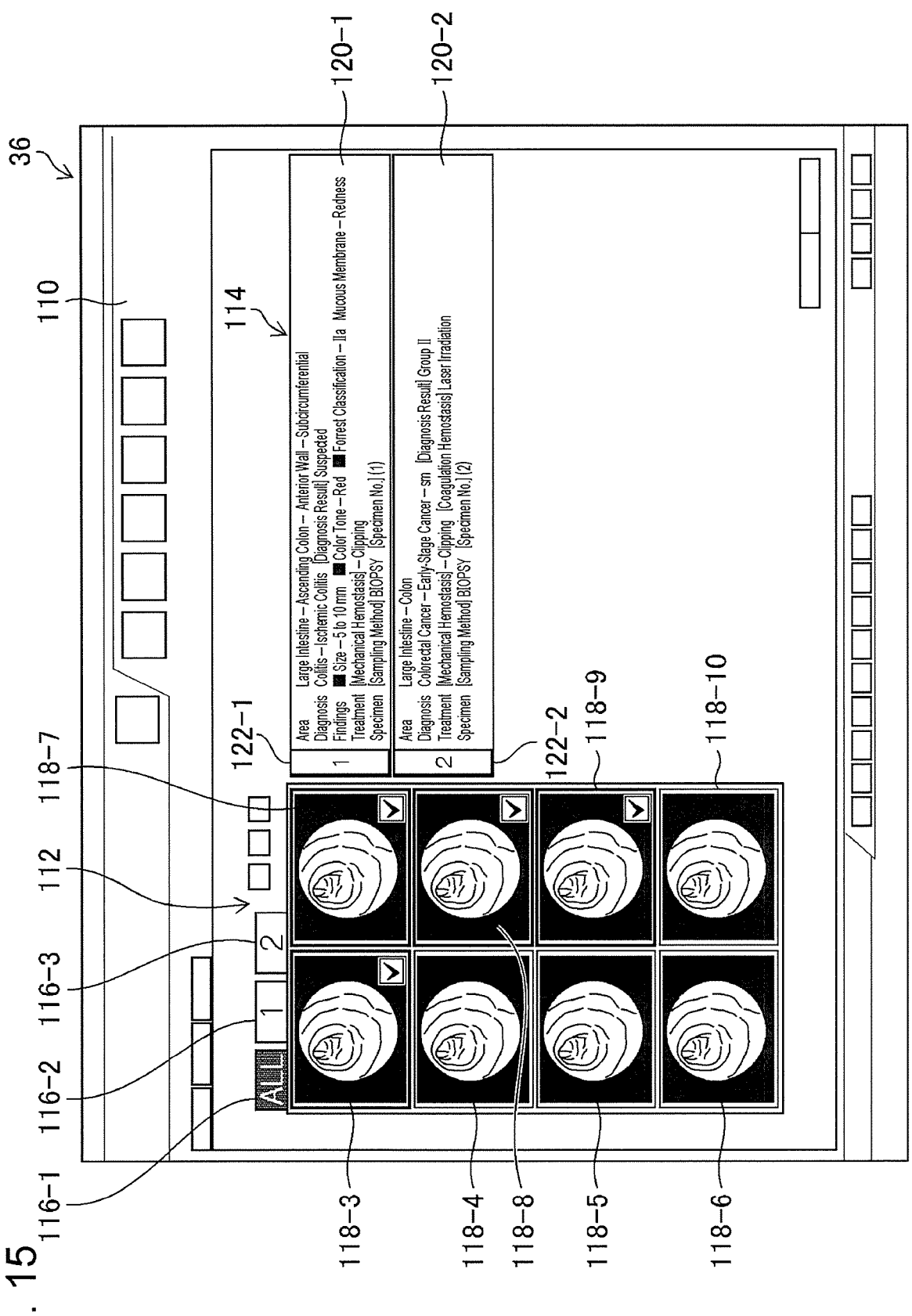
FIG. 15 is a diagram illustrating an example of the AI training image association screen.

The example of performing the drag-and-drop operation for every single examination image has been described herein. Alternatively, the drag-and-drop operation may be performed on a plurality of examination images serving as selected images. FIG. 15 is a diagram illustrating an example of a state in which examination images 118-3, 118-7, 118-8, and 118-9 are selected from among examination images 118-3 to 118-10 displayed in the image display area 112 in the AI training image association screen 110. In this case, outer frames of the examination images 118-3, 118-7, 118-8, and 118-9 are enclosed with thick lines and checkboxes of the examination images 118-3, 118-7, 118-8, and 118-9 are checked so as to allow the doctor to confirm that the examination images 118-3, 118-7, 118-8, and 118-9 are selected.

By performing the drag-and-drop operation collectively on the examination images 118-3, 118-7, 118-8, and 118-9 in this state, the examination images 118-3, 118-7, 118-8, and 118-9 can be associated with desired findings-diagnosis information through a single operation.

Figure 16:
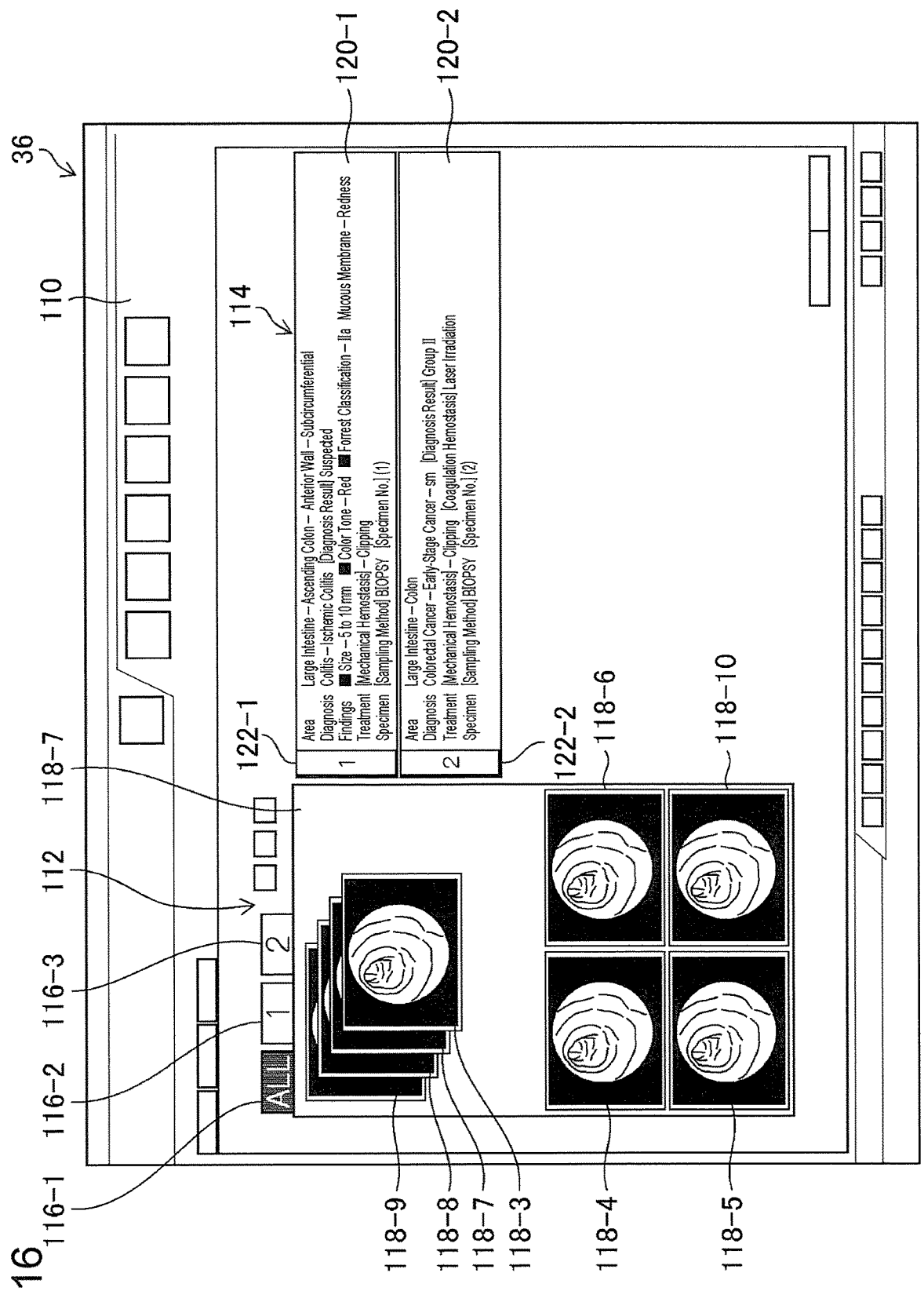
FIG. 16 is a diagram illustrating an example of the AI training image association screen.

In addition, when a plurality of examination images are selected, the selected examination images may be displayed in an overlapping manner. FIG. 16 is a diagram illustrating an example in which the selected examination images 118-3, 118-7, 118-8, and 118-9 are displayed in an overlapping manner in the AI training image association screen 110. Such overlapping display of the selected images can reduce the number of images being displayed and can implement display that allows the doctor to easily select the examination images.

As in the case illustrated in FIG. 15, by performing the drag-and-drop operation collectively on the examination images 118-3, 118-7, 118-8, and 118-9 in a state in which the examination images 118-3, 118-7, 118-8, and 118-9 are displayed in the overlapping manner, the examination images 118-3, 118-7, 118-8, and 118-9 can be associated with desired findings-diagnosis information through a single operation.

The case of performing the drag-and-drop operation on the examination images onto the findings-diagnosis information has been described herein. Alternatively, the drag-and-drop operation may be performed on the findings-diagnosis information onto the examination image.

Figure 17:
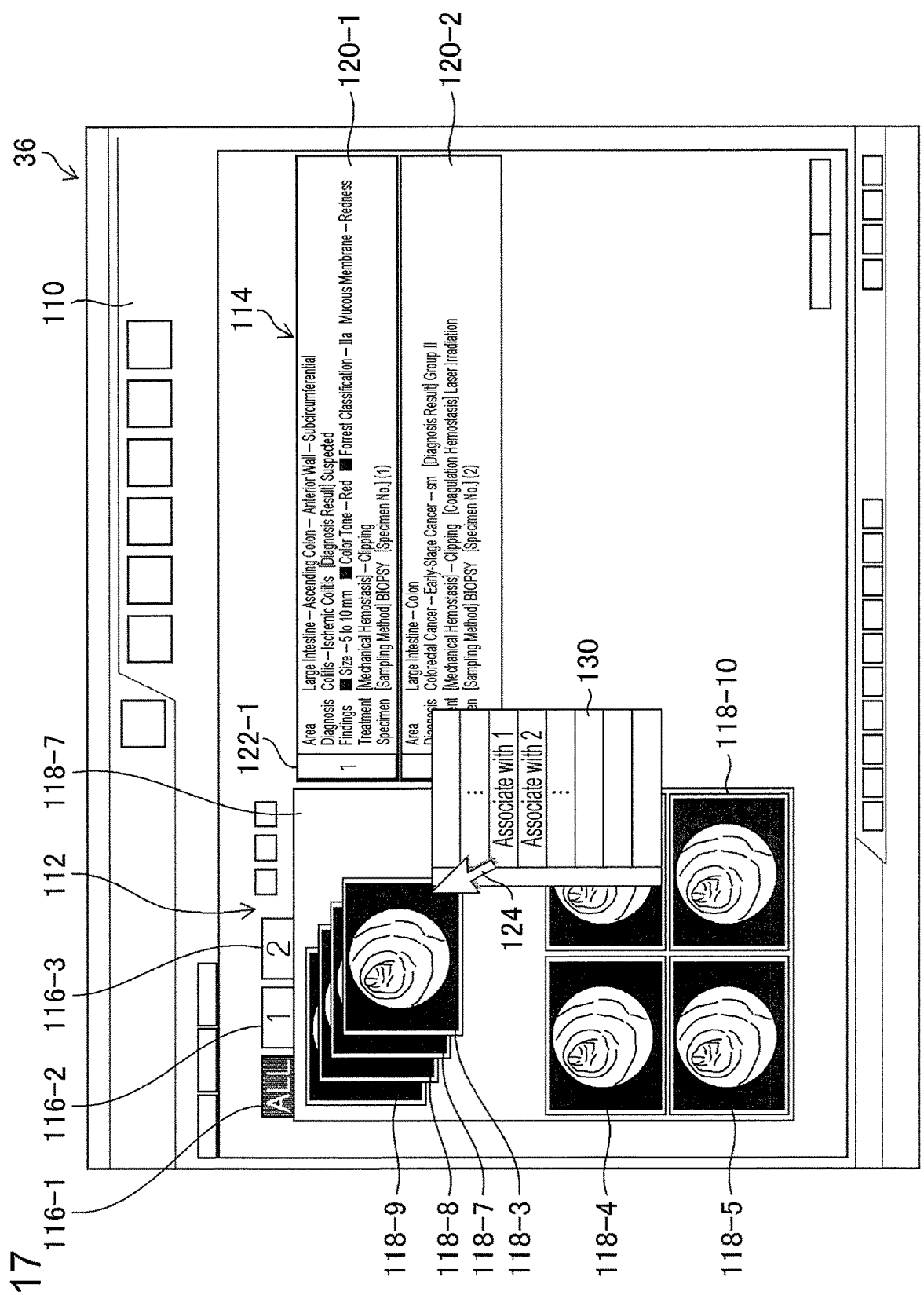
FIG. 17 is a diagram illustrating an example of the AI training image association screen.

In addition, the associating operation is not limited to the drag-and-drop operation. FIG. 17 is a diagram illustrating an example of a state in which an operation of clicking the right button of the mouse is performed after the examination images are selected in the AI training image association screen 110. In this case, the examination images 118-3, 118-7, 118-8, and 118-9 are selected. In response to the click operation performed thereafter, a right click menu 130 is displayed.

The right click menu 130 includes options such as "Associate with 1" for associating the selected examination images with the findings-diagnosis information 120-1 and "Associate with 2" for associating the selected examination images with the findings-diagnosis information 120-2.

The doctor can associate the examination images 118-3, 118-7, 118-8, and 118-9 with the findings-diagnosis information 120-1 or 120-2 by performing an operation of clicking the left button of the mouse after placing the mouse pointer at the position of the option "Associate with 1" or "Associate with 2" of the right click menu 130.

<All Image Determination Step (Step S33)>

In the all image determination step, it is determined whether or not all the examination images are associated with corresponding findings-diagnosis information. In this case, the determination is made for all the examination images displayed in the area relating to the tab 116-1. If there is an examination image not associated with the findings-diagnosis information, the process returns to step S31 and the similar processing is performed. If all the examination images are associated with the corresponding findings-diagnosis information, the process proceeds to step S34.

<All Findings-Diagnosis Information Determination Step (Step S34)>

In the all findings-diagnosis information determination step, it is determined whether or not all the pieces of findings-diagnosis information are associated with corresponding examination images. In this case, the determination is made for all the pieces of findings-diagnosis information displayed in the findings-diagnosis information display area 114. If there is findings-diagnosis information not associated with any examination image, the process returns to step S31 and the similar processing is performed.

If all the pieces of findings-diagnosis information are associated with corresponding examination images, the recording control unit 88 causes the endoscopy management server 40 (an example of a recording apparatus) to record therein, as training data, the associated examination images and findings-diagnosis information (an example of a recording control step), and ends the processing of this flowchart to end the AI training image association step.

Note that an endoscopic image and findings-diagnosis information may be sequentially recorded in the endoscopy management server 40 when the endoscopic image and the findings-diagnosis information are associated with each other. In addition, even if all the examination images are not associated with corresponding findings-diagnosis information or all the pieces of findings-diagnosis information are not associated with corresponding examination images, the AI training image association step may be ended.

[Details of Pathological Examination Requesting Step]

Figure 18:
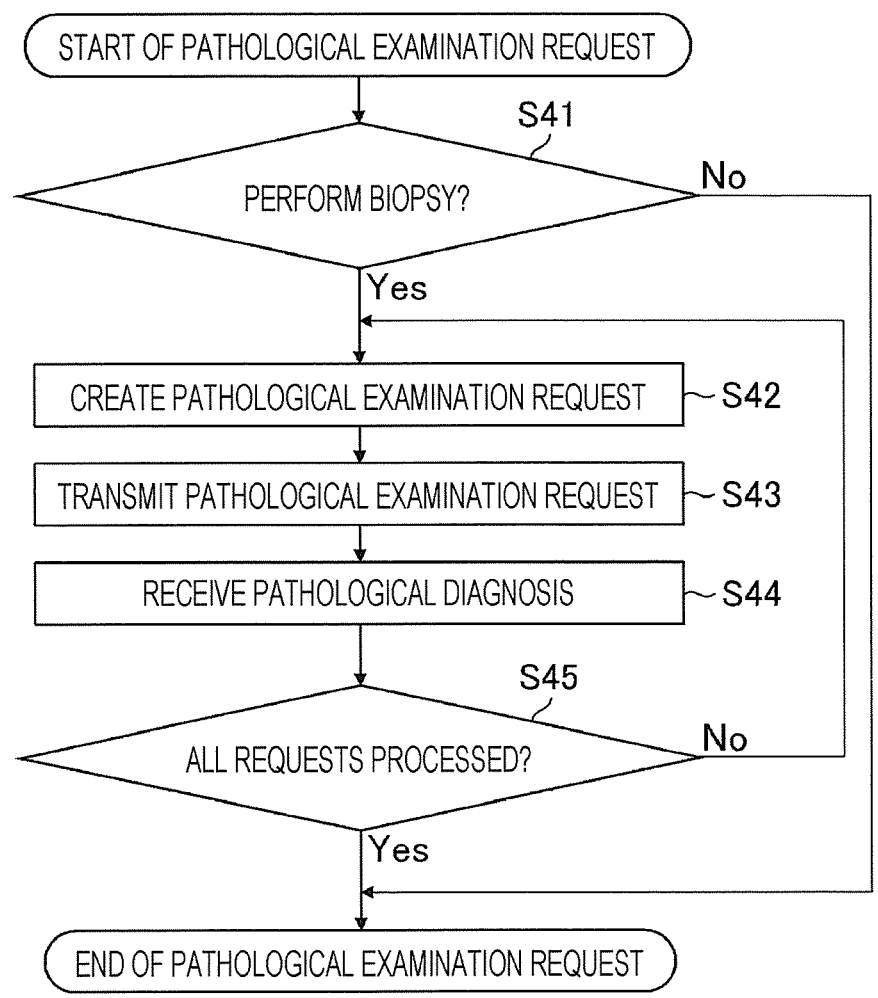
FIG. 18 is a flowchart illustrating detailed processing of a pathological examination requesting step.

In the pathological examination requesting step, a request form of pathological diagnosis to be performed on a pathological specimen sampled during an endoscopic examination is created and a pathological diagnosis result is acquired. FIG. 18 is a flowchart illustrating detailed processing of the pathological examination requesting step. The pathological examination requesting step includes a whether-to-perform biopsy determination step (step S41), a pathological examination request creation step (step S42), a pathological examination request transmission step (step S43), a pathological diagnosis reception step (step S44), and an all pathological examination request end determination step (step S45).

<Whether-to-Perform Biopsy Determination Step (Step S41)>

In the whether-to-perform biopsy determination step, the doctor determines whether or not there is a specimen for pathological diagnosis. If there is no specimen for pathological diagnosis, the processing of this flowchart is ended to end the pathological examination requesting step. If there is a specimen for pathological diagnosis, the process proceeds to step S42.

<Pathological Examination Request Creation Step (Step S42)>

In the pathological examination request creation step, the doctor creates a pathological examination request for the pathological specimen acquired in the endoscopic examination, by using the endoscopy management report terminal 32, based on endoscopic findings and information for identifying the pathological specimen.

<Pathological Examination Request Transmission Step (Step S43)>

In the pathological examination request transmission step, the pathological examination request created in the pathological examination request creation step is transmitted to the electronic medical chart system 22 via the order gateway 70. The electronic medical chart system 22 manages the received pathological examination request as an order and requests the pathology system 24 to make a pathological diagnosis.

<Pathological Diagnosis Reception Step (Step S44)>

In the pathological diagnosis reception step, a pathological diagnosis result of a pathological examination which has been requested by the pathology system gateway 72 and for which the pathological diagnosis result has not been received is received from the pathology system 24, and is transmitted to the endoscopy management server 40. The endoscopy management server 40 stores the received pathological diagnosis result in association further with the examination image and the findings-diagnosis information that are associated with each other.

<All Pathological Examination Request End Determination Step (Step S45)>

In the all pathological examination request end determination step, it is determined whether or not the pathological examination request has been performed for all the acquired pathological specimens. If there is a pathological specimen for which the pathological examination request has not been made, the process returns to step S42 and the similar processing is repeated. If the pathological examination request has been made for all the pathological specimens, the processing of this flowchart is ended to end the pathological examination requesting step.

[Details of AI Training Data Output Step]

Figure 19:
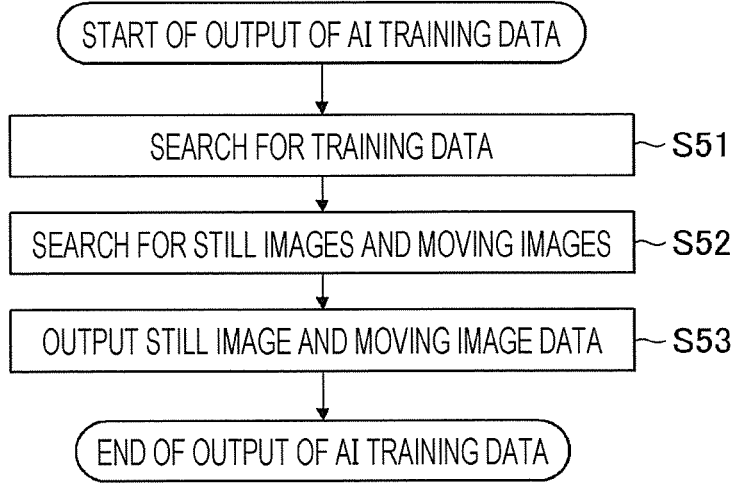
FIG. 19 is a flowchart illustrating detailed processing of an AI training data output step.

In the AI training data output step, examination images and corresponding findings-diagnosis information that are associated with each other in the AI training image association step are output as training data. FIG. 19 is a flowchart illustrating detailed processing of the AI training data output step. The AI training data output step includes a training data search step (step S51), a still image and moving image search step (step S52), and a still image and moving image data output step (step S53).

<Training Data Search Step (Step S51)>

In the training data search step, the AI training data output gateway 74 searches training data recorded in the endoscopy management server 40 for yet-to-be-learned training data with which training has not been performed by the training unit 64. For example, the AI training data output gateway 74 extracts a difference between training data recorded in the endoscopy management server 40 immediately before a timing of moment of the previous transmission of the training data to the AI engine 52 and training data recorded in the endoscopy management server 40 at present to search for training data with which training has not been performed by the training unit 64.

<Still Image and Moving Image Search Step (Step S52)>

In the still image and moving image search step, the AI training data output gateway 74 searches still images recorded in the endoscopy management server 40 and the moving images recorded in the moving-image storing NAS 46 for still images and moving images of the yet-to-be-learned training data retrieved in the training data search step.

<Still Image and Moving Image Data Output Step (Step S53)>

In the still image and moving image data output step, the AI training data output gateway 74 transmits, to the AI engine 52, data of the still images and moving images retrieved in the still image and moving image search step and findings-diagnosis information associated with the still images and moving images. When the pathological diagnosis result is associated, the AI training data output gateway 74 also transmits the pathological diagnosis result to the AI engine 52. The transmitted data of the still images and the like is input to the training unit 64 from the training data input unit 62.

<AI Training Step (Step S60)>

In the AI training step, the training unit 64 trains a model using the training data input to the training data input unit 62. The trained model that has been trained by the training unit 64 is input to the discrimination unit 58, and the model in the discrimination unit 58 is updated to the trained model.

As described above, in accordance with the present embodiment, a model can be appropriately trained.

Second Embodiment

[Input of Lesion Position Information]

In a second embodiment, information on a lesion position in examination images is further included in training data. A doctor inputs the lesion position information using the endoscopy management report terminal 32. In the present embodiment, the lesion position is recorded using a bounding box. A bounding box is a quadrangular region including a lesion, and is designated by at least two coordinate positions herein.

Figure 20:
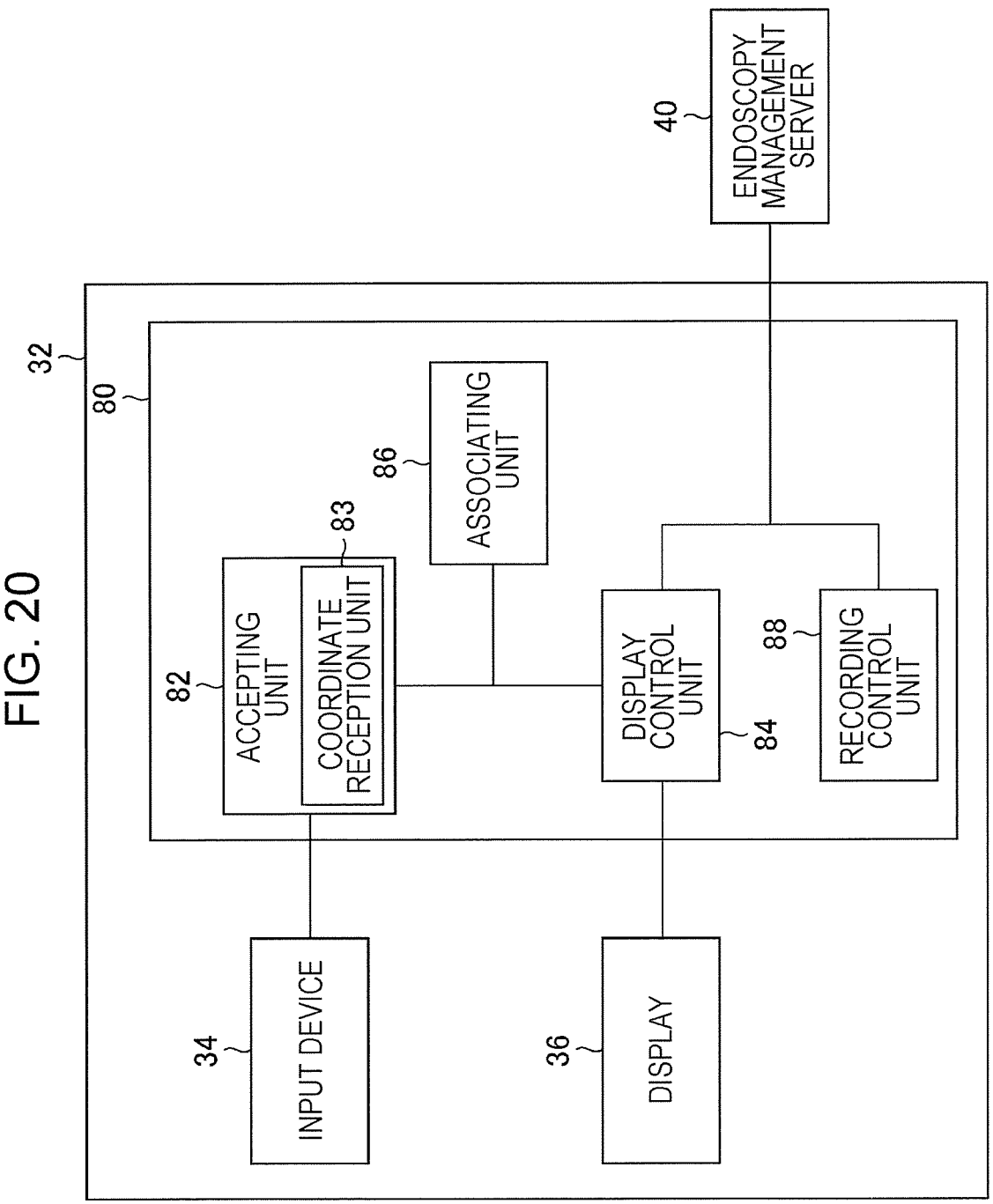
FIG. 20 is a block diagram illustrating an example of the configuration of the endoscopy management report terminal.

FIG. 20 is a block diagram illustrating an example of a configuration of the endoscopy management report terminal 32 according to the second embodiment. Note that portions that are in the block diagram of FIG. 2 in common are assigned the same reference signs to omit detailed description thereof.

The accepting unit 82 of the endoscopy management report terminal 32 includes a coordinate reception unit 83. The coordinate reception unit 83 receives and accepts at least two coordinate positions on the bounding box input from the input device 34.

Figure 21:
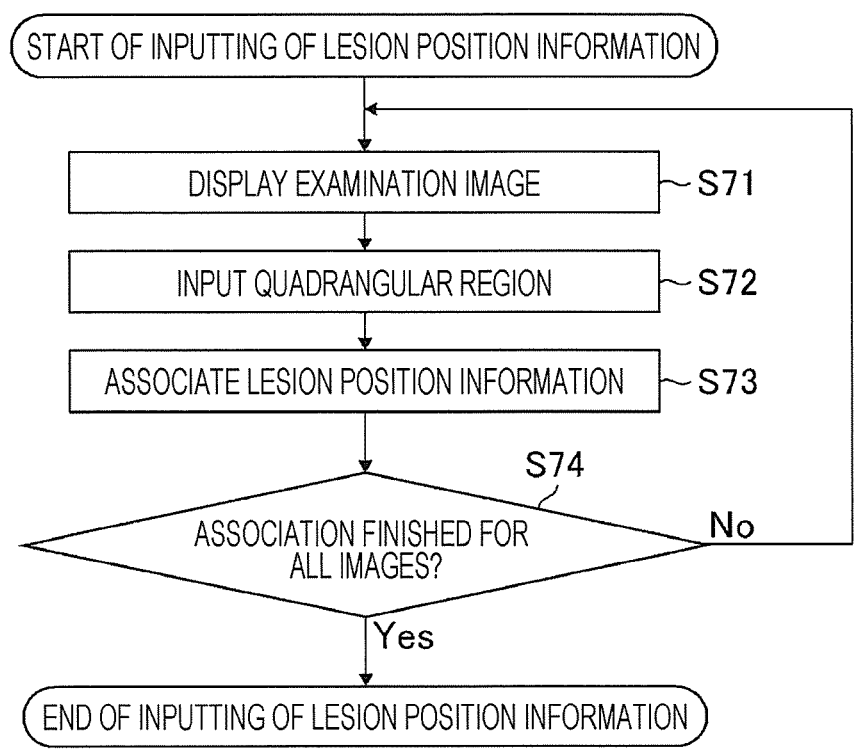
FIG. 21 is a flowchart illustrating a process of a lesion position information input method.

FIG. 21 is a flowchart illustrating a process of a lesion position information input method. A method of sequentially inputting lesion position information for a plurality of examination images captured in a single endoscopic examination will be described herein. The lesion position information input method includes an examination image display step (step S71), a quadrangular region input step (step S72), a lesion position information association step (step S73), and an end determination step (step S74).

<Examination Image Display Step (Step S71)>

In the examination image display step, the display control unit 84 causes the display 36 to display an examination image of the corresponding endoscopic examination from among examination images recorded in the endoscopy management server 40.

Figure 22:
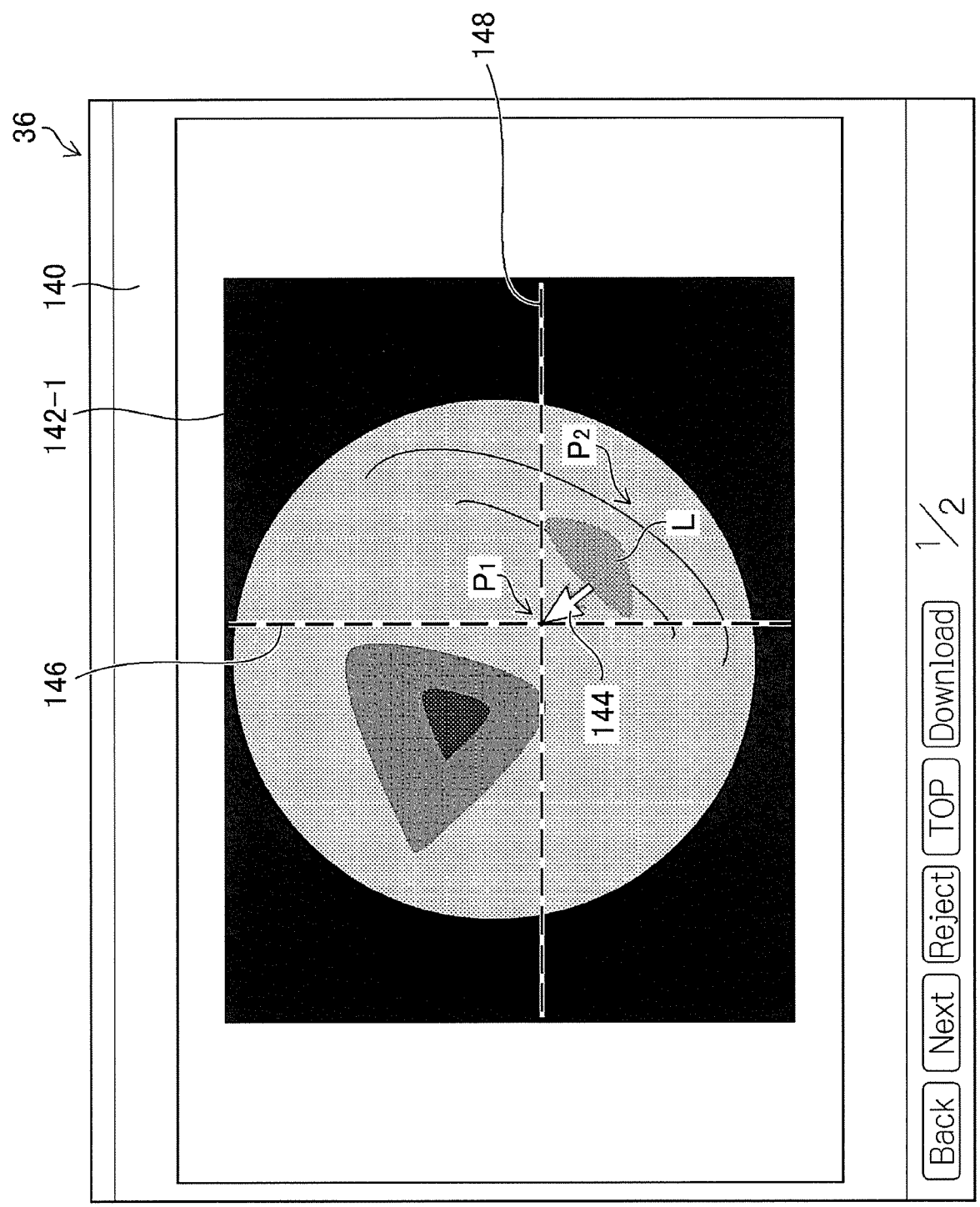
FIG. 22 is a diagram illustrating an example of a lesion position information input screen.

FIG. 22 is a diagram illustrating an example of a lesion position information input screen 140 displayed on the display 36. The lesion position information is input in the lesion position information input screen 140. An examination image 142-1 is displayed in the lesion position information input screen 140 illustrated in FIG. 22. In addition, the examination image 142-1 includes a lesion L.

<Quadrangular Region Input Step (Step S72)>

In the quadrangular region input step, the doctor inputs a quadrangular region including the position of the lesion in the examination image displayed on the display 36. The quadrangular region is input by designating a first point that is the upper left point of the quadrangular region and further designating a second point that is the lower right point and is at the diagonal angle of the first point of the quadrangular region. The first point and the second point are designated through, for example, an operation of a mouse of the input device 34 or an operation on a touch panel of the input device 34 with a finger.

FIGS. 22 to 25 are diagrams illustrating an example of inputting a quadrangular region through an operation of a mouse in the lesion position information input screen 140. It is assumed that a position $P_1$ and a position $P_2$ respectively denote the upper left position and the lower right position of a quadrangular region including the lesion L and having the smallest area in the examination image 142-1. A case of inputting the quadrangular region whose upper left position and lower right position are the position $P_1$ and the position $P_2$, respectively, will be described herein.

The display control unit 84 causes a mouse pointer 144, a guide line 146, and a guide line 148 to be displayed in the lesion position information input screen 140. That is, the mouse pointer 144 is displayed in the lesion position information input screen 140 as illustrated in FIG. 22. In addition, the guide line 146 extending in the vertical direction and the guide line 148 extending in the horizontal direction are displayed in the lesion position information input screen 140 to make it easier to perceive the vertical-direction position and the horizontal-direction position of the mouse pointer 144. The intersection point of the guide lines 146 and 148 is the position of the mouse pointer 144.

Figure 23:
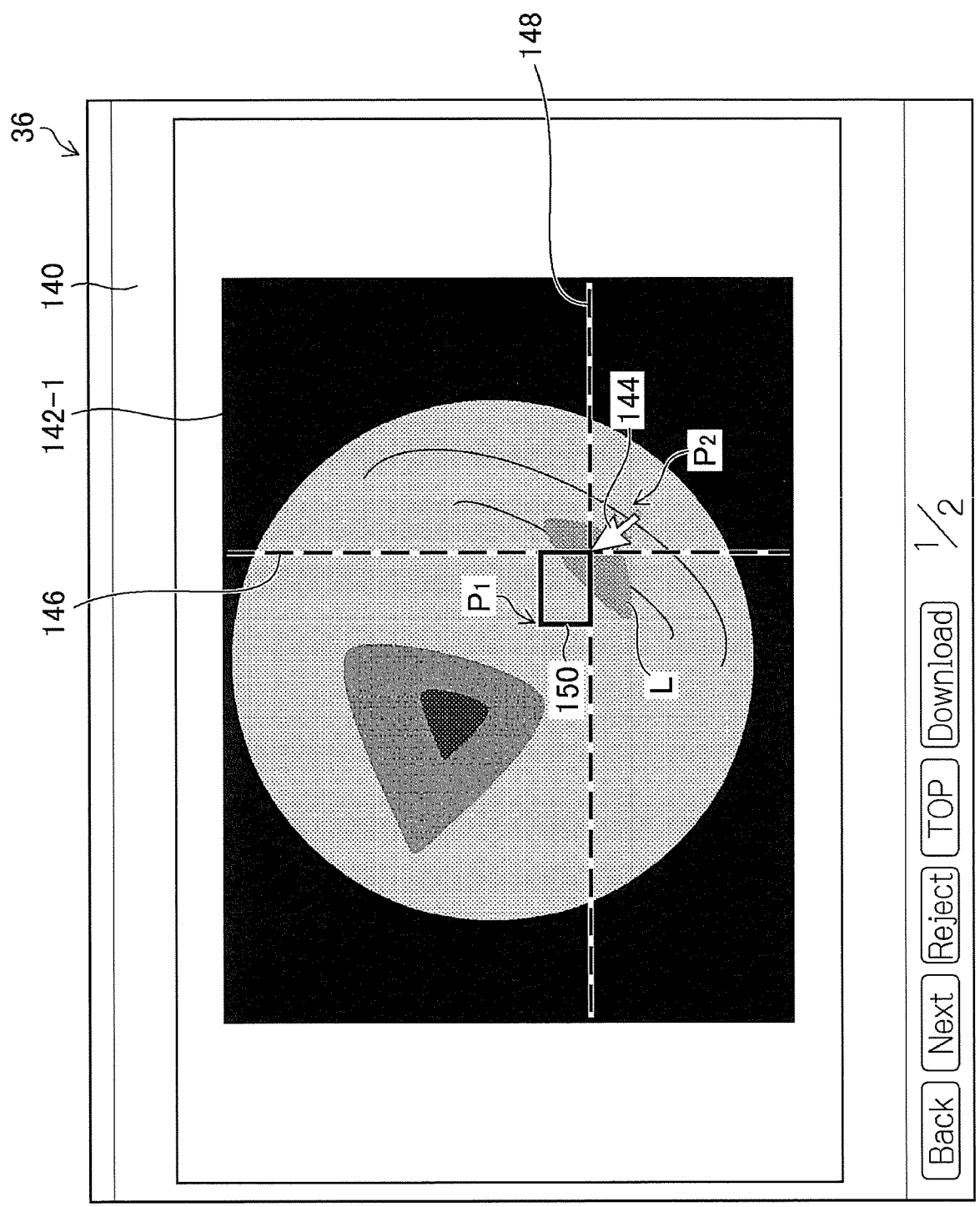
FIG. 23 is a diagram illustrating an example of the lesion position information input screen.

When the doctor inputs a quadrangular region, the doctor first moves the mouse pointer 144 to the position $P_1$ as illustrated in FIG. 22. The doctor then performs a click operation of pressing the left button of the mouse in a state in which the mouse pointer 144 is placed at the position $P_1$, and performs a drag operation of moving the mouse pointer 144 to the position $P_2$ while maintaining the click operation. FIG. 23 is a diagram illustrating a state of the drag operation from the position $P_1$ to the position $P_2$. As illustrated in FIG. 23, a quadrangle 150 having the drag start position (the position $P_1$ in this case) and the current position of the mouse pointer 144 at the diagonal angles is displayed during the drag operation.

Figure 24:
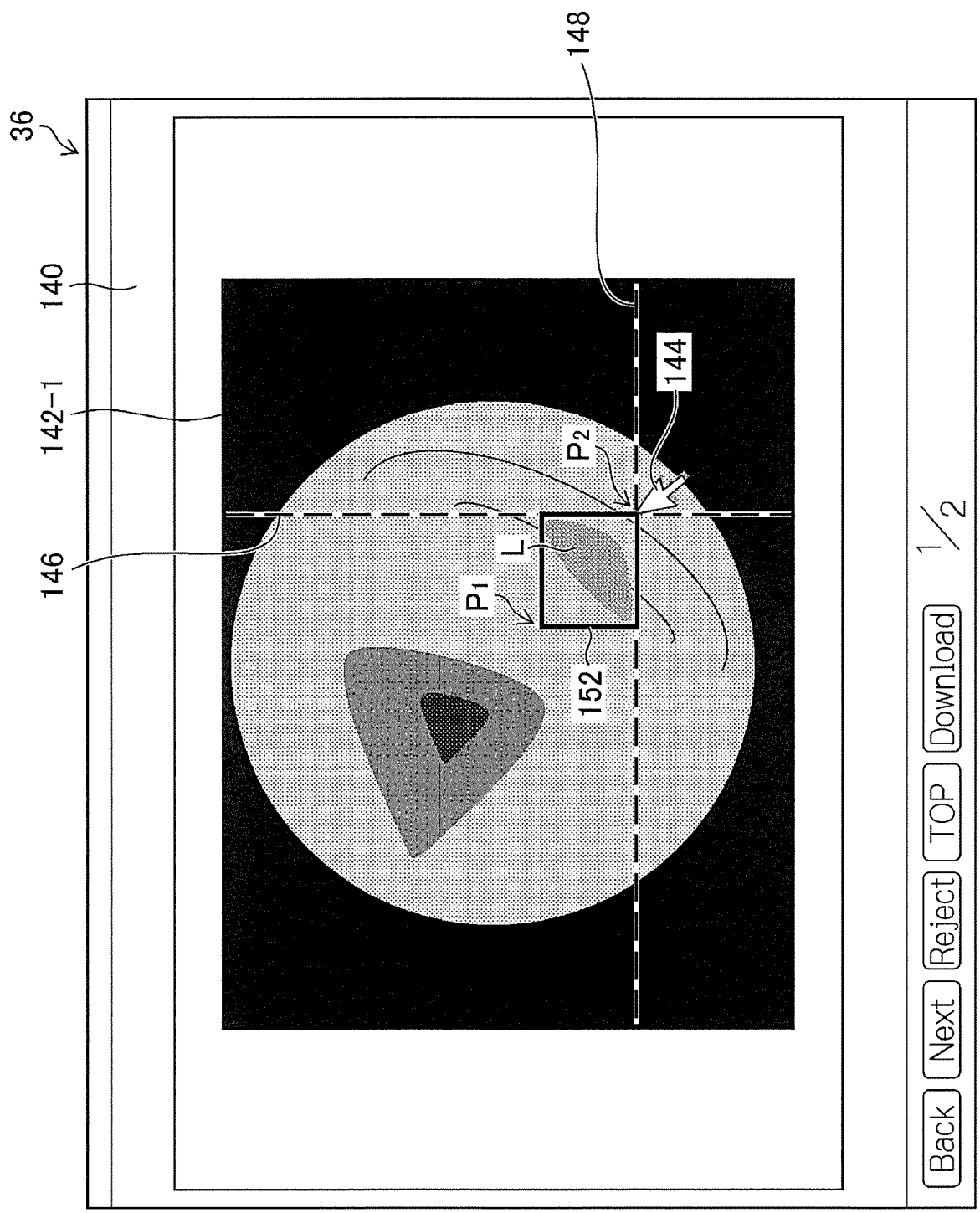
FIG. 24 is a diagram illustrating an example of the lesion position information input screen.

After further continuing the drag operation and moving the mouse pointer 144 to the position $P_2$ as illustrated in FIG. 24, the doctor stops the click operation of the mouse in a state in which the mouse pointer 144 is placed at the position $P_2$.

In response to this operation, the quadrangle 150 whose upper left position and lower right position are the position $P_1$ and the position $P_2$, respectively, is set as a bounding box 152. The coordinate reception unit 83 of the accepting unit 82 receives coordinates $(X_1, Y_1)$ of the upper left position $P_1$ of the bounding box 152 on the display 36 and coordinates $(X_2, Y_2)$ of the lower right position $P_2$ of the bounding box 152 on the display 36.

A quadrangular region including the lesion L and having the minimum area is input in this case. Alternatively, a quadrangular region not having the minimum area may be input as long as the quadrangular region includes the lesion L.

In the case of inputting the quadrangular region using a touch panel, for example, the doctor may touch the position serving as the first point of the quadrangular region, move the finger to the position serving as the second point of the quadrangular region while keeping the finger in contact with the touch panel, and then separate the finger from the touch panel. In addition, the doctor may simultaneously designate the first point and the second point with two fingers.

<Lesion Position Information Association Step (Step S73)>

In the lesion position information association step, the associating unit 86 calculates the lesion position information from the quadrangular region input in the quadrangular region input step, and associates the calculated lesion position information with the examination image.

The associating unit 86 acquires coordinates, on the display 36, of the examination image 142-1 which the display control unit 84 has caused the display 36 to display. The associating unit 86 calculates coordinates of the bounding box 152 in the examination image 142-1 as the lesion position information, based on the coordinates of this examination image 142-1 on the display 36 and the coordinates of the bounding box 152 on the display 36.

The recording control unit 88 causes the endoscopy management server 40 to record therein the calculated lesion position information in association with the examination image.

<End Determination Step (Step S74)>

Figure 25:
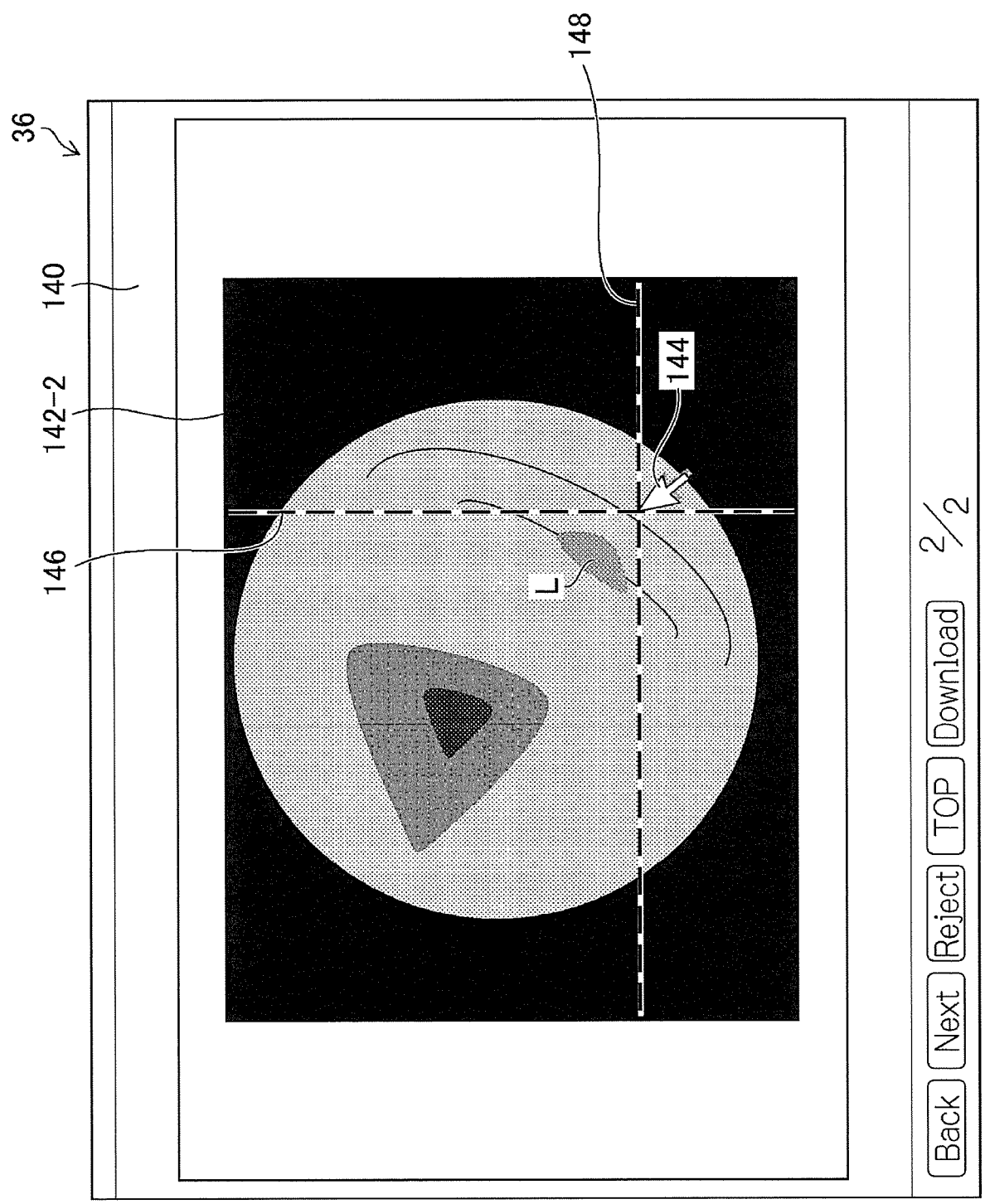
FIG. 25 is a diagram illustrating an example of the lesion position information input screen.

In the end determination step, it is determined whether or not all the examination images have been associated with the corresponding lesion position information. If there is an examination image that is not associated with the lesion position information, the process returns to step S71 and the similar processing is repeated. That is, as illustrated in FIG. 25, the display control unit 84 causes an examination image 142-2, which is the next examination image of the examination image 142-1, to be displayed on the display 36.

The examination image 142-2 is displayed upon the doctor ending inputting of the quadrangular region in the examination image 142-1 after ending the drag operation in the quadrangular region input step. Displaying the next examination image without waiting for an operation other than the end of the drag operation in this manner enables the quadrangular region to be quickly input. Note that the next examination image may be displayed in response to clicking of a button or the like for causing the next examination image to be displayed after the end of the drag operation. Displaying the next examination image in this manner enables a plurality of quadrangular regions to be input for a single image.

If all the examination images are associated with the corresponding lesion position information, the processing of this flowchart ends.

In the present embodiment, the lesion position information may be input, for example, prior to the AI training image selection step (step S31) of the first embodiment. It is also conceived that the lesion position information is input only for the examination images associated with the findings-diagnosis information after the association step (step S32). The similar processing may be performed in the lesion marking step (step S22).

It is also conceived that a search may be performed in the training data search step (step S51) upon condition that the lesion position information is added. It is also conceived that the area of the lesion position information is used as the search condition.

In the present embodiment, the first point and the second point of the quadrangular region are designated as the upper left position and the lower right position, respectively. However, the designated positions and the designation order are not limited as long as two diagonal points can be designated. In addition, the quadrangular region may have rounded corners. The lesion position information may be input using a circular region.

Figure 26:
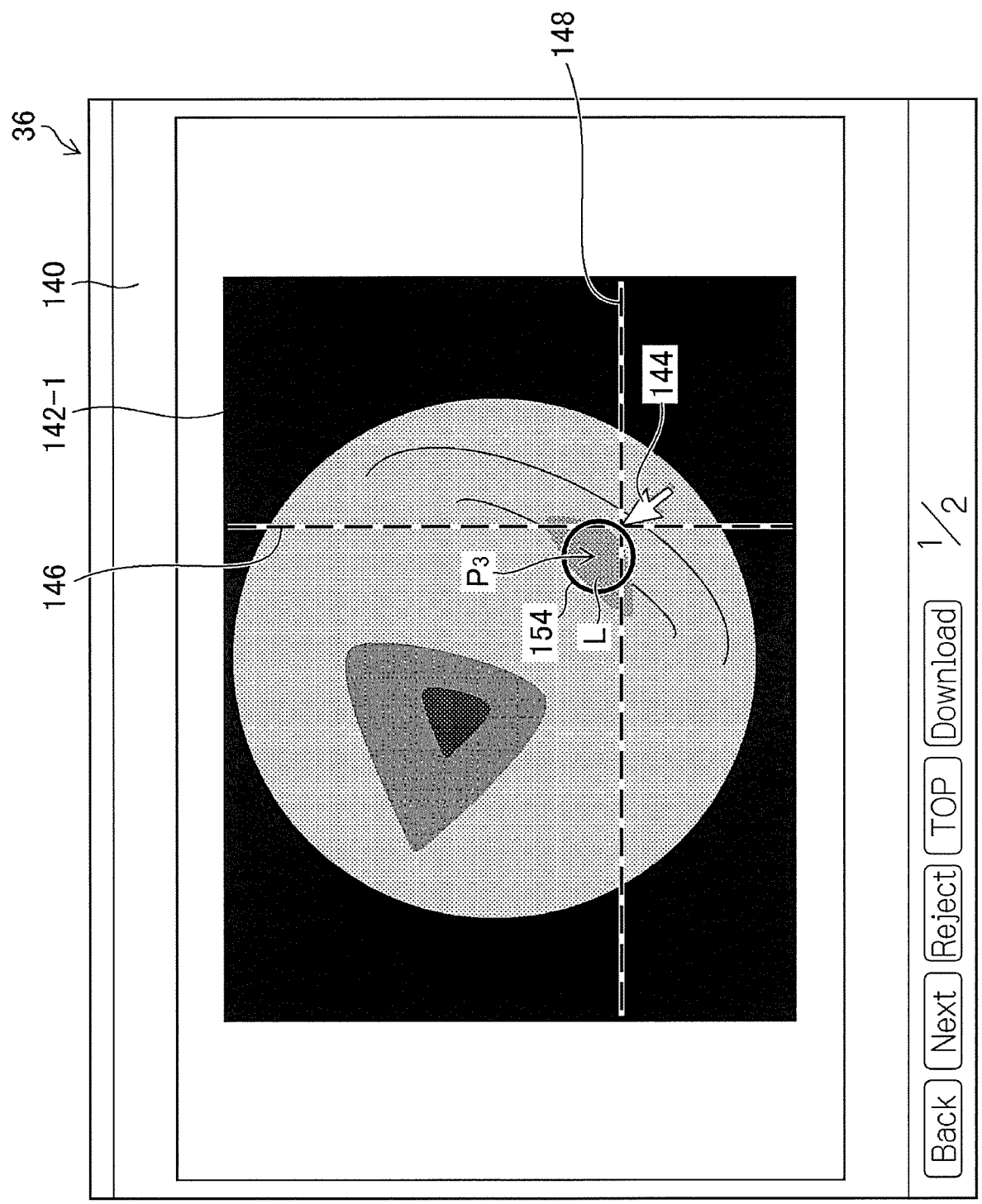
FIG. 26 is a diagram illustrating an example of the lesion position information input screen.

FIG. 26 is a diagram illustrating an example of inputting a circular region. When a drag operation is performed by pressing the left button of the mouse in a state in which the mouse pointer 144 is placed at a position $P_3$ that is the center position of the lesion L, a circular region 154 centered at the position $P_3$ extends. The circular region can be input by placing this circular region 154 at the position including the lesion L and then stopping the drag operation.

The associating unit 86 converts the center coordinates of the circular region 154 on the display 36 and the distance from the center coordinates (radius of the circular region) into the center coordinates in the examination image 142-1 and the distance from the center coordinates to obtain the lesion position information.

Alternatively, an elliptic region may be input by designating three points. In this case, it is conceived that the first point is designated as the center coordinates, the second point is designated to indicate the distance from the center coordinates in the horizontal direction, and the third point is designated to indicate the distance from the center coordinates in the vertical direction, or the like.

Figure 27:
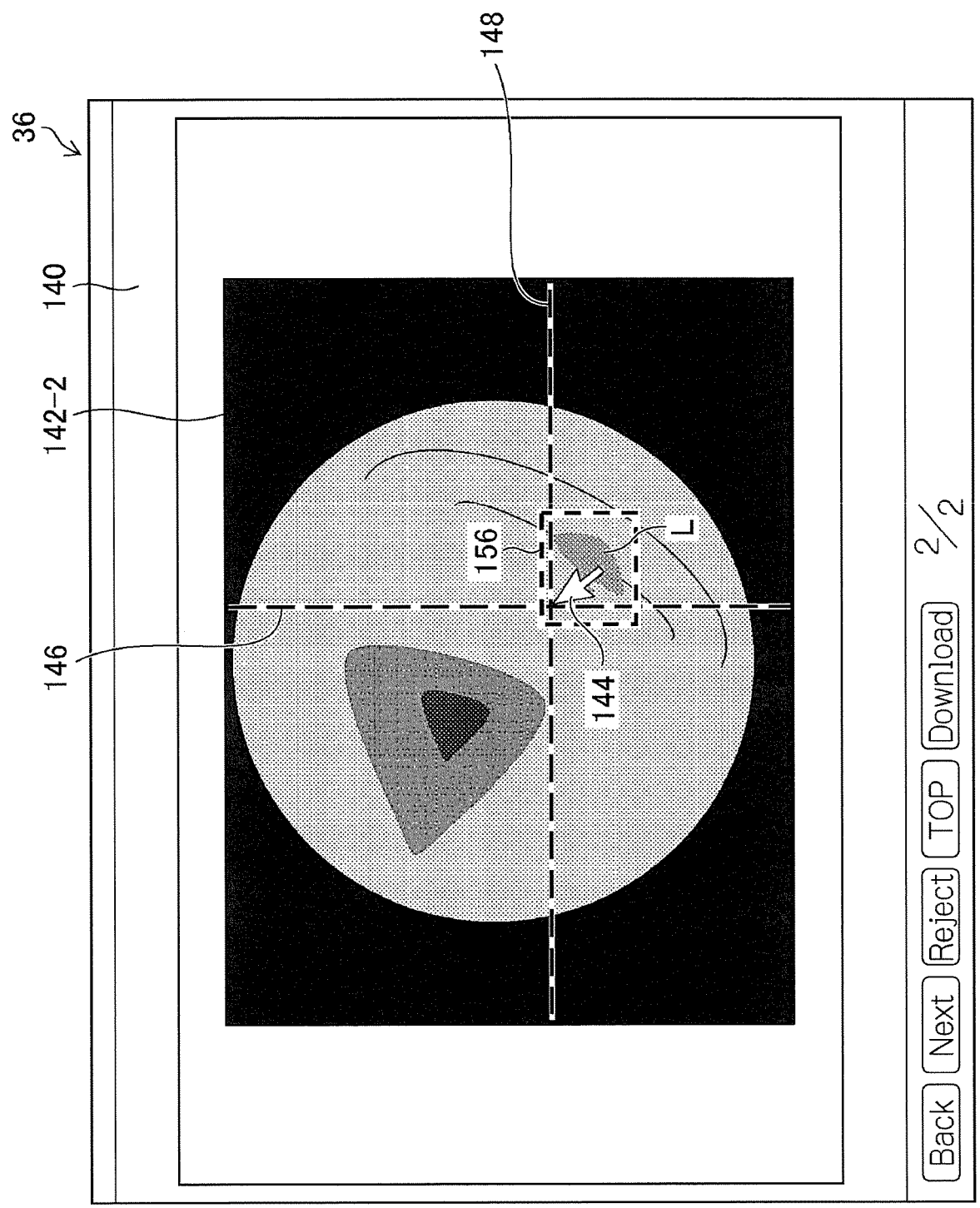
FIG. 27 is a diagram illustrating an example of the lesion position information input screen.
Figure 28:
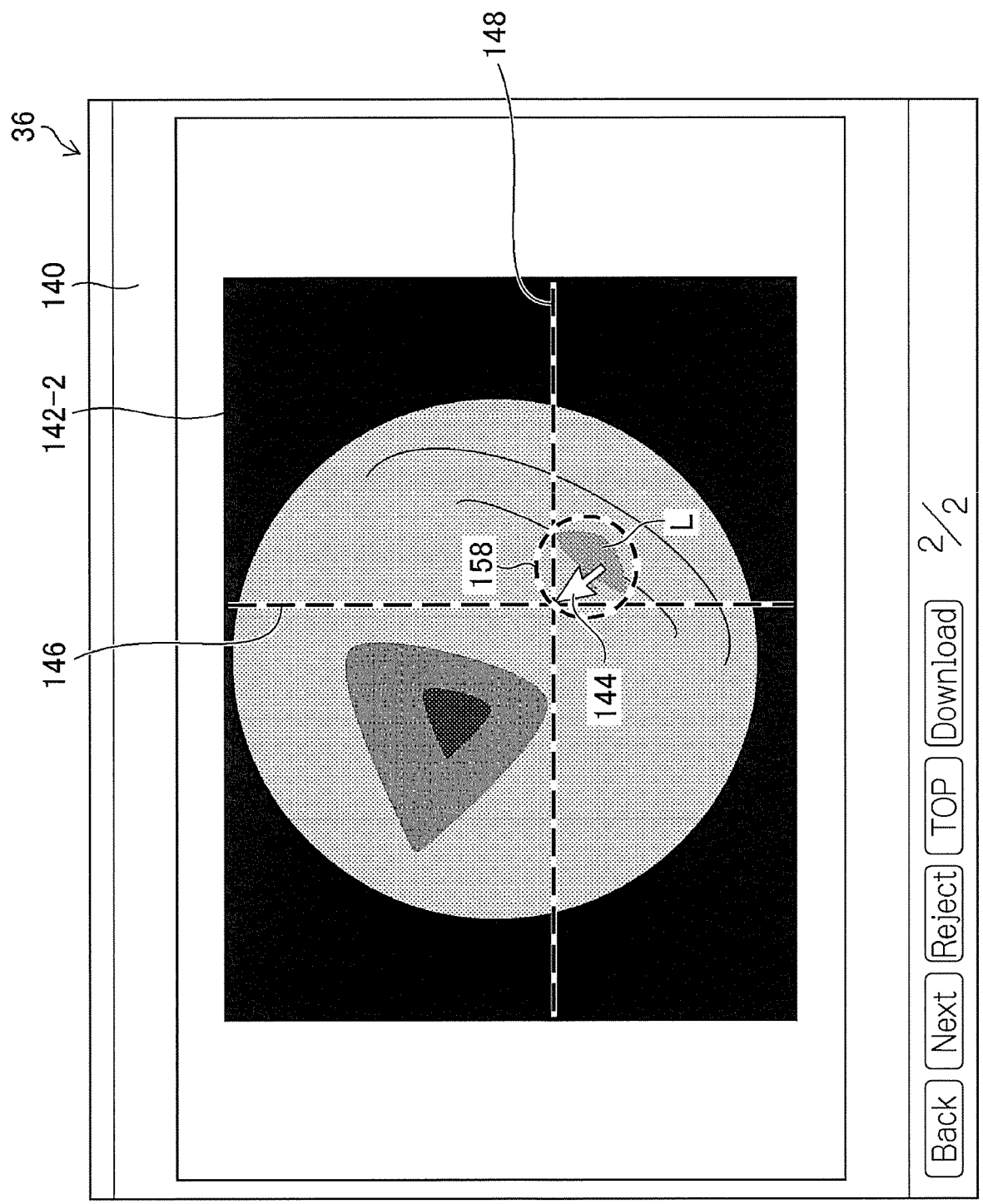
FIG. 28 is a diagram illustrating an example of the lesion position information input screen.

Further, when a new examination image is displayed in the examination image display step, the bounding box used for inputting the quadrangular region in the immediately preceding examination image may be displayed. In the example illustrated in FIG. 27, a bounding box 156 for the first examination image 142-1 is displayed when the quadrangular region is input for the second examination image 142-2. In addition, in the example illustrated in FIG. 28, a circular region 158 for the first examination image 142-1 is displayed when the circular region is input for the second examination image 142-2.

The same lesion is often shown in the similar size at the similar position. Thus, displaying the position designated before as a guide makes it easier to designate the position of the lesion.

Third Embodiment

An endoscope apparatus will be described which includes a medical image processing apparatus that analyzes a medical image using the trained model generated in the first embodiment.

Figure 29:
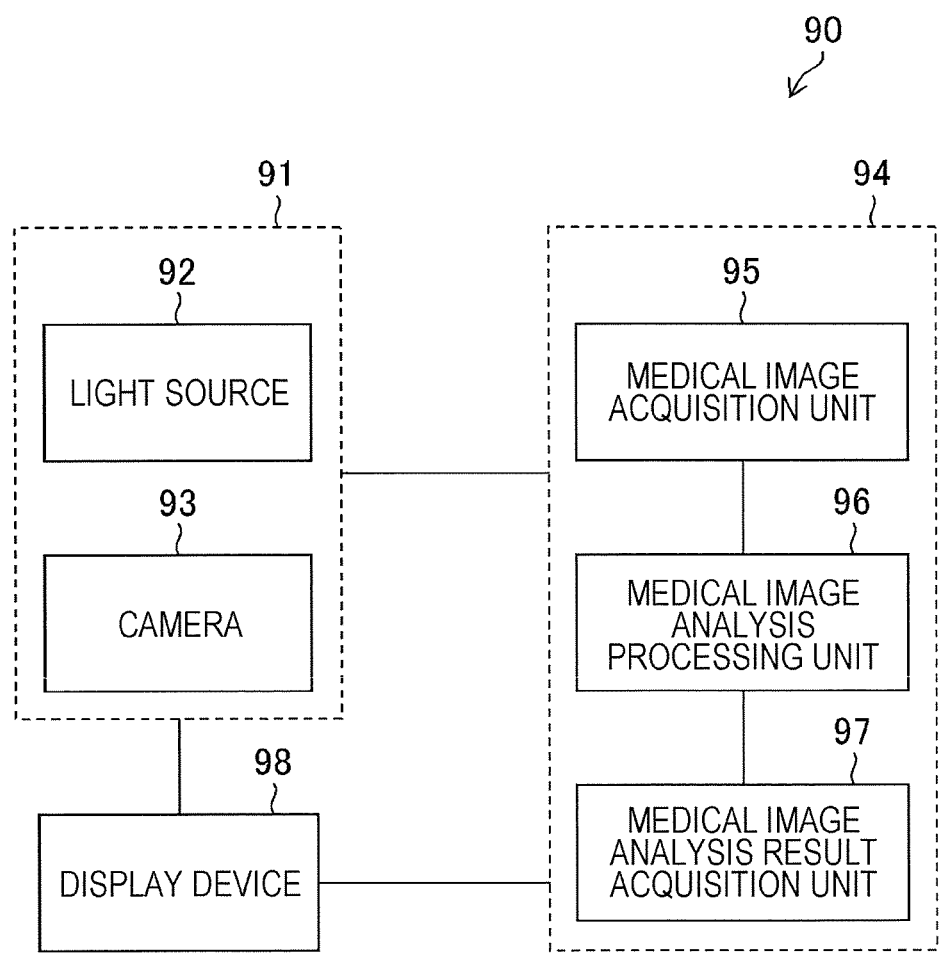
FIG. 29 is a block diagram illustrating an example of a configuration of an endoscope apparatus.

FIG. 29 is a block diagram illustrating an example of a configuration of an endoscope apparatus 90. The endoscope apparatus 90 is connected to, for example, the endoscopy department local LAN 30 (see FIG. 1). The endoscope apparatus 90 includes an endoscope 91, a medical image processing apparatus 94, and a display device 98.

The endoscope 91 includes a light source 92 and a camera 93. The light source 92 irradiates a part to be observed in the body cavity of a patient with irradiation light. The camera 93 receives light that is reflected off the part to be observed to capture an endoscopic image of the part to be observed.

The medical image processing apparatus 94 (an example of an endoscopic image processing apparatus) includes a medical image acquisition unit 95, a medical image analysis processing unit 96, and a medical image analysis result acquisition unit 97.

The medical image acquisition unit 95 acquires a medical image. In the present embodiment, the medical image acquisition unit 95 acquires an endoscopic image captured by the endoscope 91.

The medical image analysis processing unit 96 analyzes the medical image acquired by the medical image acquisition unit 95. In the present embodiment, a lesion is discriminated from the endoscopic image using the trained model generated in the first embodiment.

The medical image analysis result acquisition unit 97 acquires the analysis result obtained by the medical image analysis processing unit 96.

For example, a liquid crystal monitor is used as the display device 98. The display device 98 displays the endoscopic image captured by the endoscope 91 and the analysis result acquired by the medical image analysis result acquisition unit 97. In the present embodiment, the region of the discriminated lesion is colored and is displayed to be superimposed on the endoscopic image. The lesion region may be surrounded by a frame and may be displayed in a superimposed manner.

The endoscope apparatus 90 thus configured discriminates, using the trained model, a lesion from an endoscopic image that is being captured, and allows the doctor who performs an endoscopic examination to recognize the lesion.

The case where the medical image processing apparatus 94 is included in the endoscope apparatus 90 has been described herein. Alternatively, the medical image processing apparatus 94 may be included in the endoscopy management report terminal 32 or the video capturing terminal 38.

APPENDICES

In addition to the embodiments and examples described above, configurations described below are also included in the scope of the present invention.

Appendix 1

A medical image processing apparatus wherein
a medical image analysis processing unit detects a region of interest that is a region to be focused on, based on a feature quantity of pixels of a medical image, and
a medical image analysis result acquisition unit acquires an analysis result obtained by the medical image analysis processing unit.

Appendix 2

A medical image processing apparatus wherein
a medical image analysis processing unit detects whether there is a target to be focused on, based on a feature quantity of pixels of a medical image, and
a medical image analysis result acquisition unit acquires an analysis result obtained by the medical image analysis processing unit.

Appendix 3

The medical image processing apparatus wherein
the medical image analysis result acquisition unit
acquires the analysis result of the medical image from a recording apparatus in which the analysis result is recorded, and
the analysis result indicates either the region of interest that is a region to be focused on and that is included in the medical image or whether or not there is the target to be focused on, or indicates both of the region of interest and whether or not there is the target to be focused on.

Appendix 4

The medical image processing apparatus wherein the medical image is a normal-light image obtained by radiating light in a white range or light in a plurality of wavelength ranges as the light in the white range.

Appendix 5

The medical image processing apparatus wherein
the medical image is an image obtained by radiating light in a particular wavelength range, and
the particular wavelength range is a range narrower than a white wavelength range.

Appendix 6

The medical image processing apparatus wherein the particular wavelength range is a blue or green range in a visible range.

Appendix 7

The medical image processing apparatus wherein the particular wavelength range includes a wavelength range of 390 nm or greater and 450 nm or less or a wavelength range of 530 nm or greater and 550 nm or less, and the light in the particular wavelength range has a peak wavelength in the wavelength range of 390 nm or greater and 450 nm or less or the wavelength range of 530 nm or greater and 550 nm or less.

Appendix 8

The medical image processing apparatus wherein the particular wavelength range is a red range in a visible range.

Appendix 9

The medical image processing apparatus wherein the particular wavelength range includes a wavelength range of 585 nm or greater and 615 nm or less or a wavelength range of 610 nm or greater and 730 nm or less, and the light in the particular wavelength range has a peak wavelength in the wavelength range of 585 nm or greater and 615 nm or less or the wavelength range of 610 nm or greater and 730 nm less.

Appendix 10

The medical image processing apparatus wherein the particular wavelength range includes a wavelength range in which a light absorption coefficient is different between oxyhemoglobin and deoxyhemoglobin, and the light in the particular wavelength range has a peak wavelength in the wavelength range in which the light absorption coefficient is different between oxyhemoglobin and deoxyhemoglobin.

Appendix 11

The medical image processing apparatus wherein the particular wavelength range includes a wavelength range of 400±10 nm, a wavelength range of 440±10 nm, a wavelength range of 470±10 nm, or a wavelength range of 600 nm or greater and 750 nm or less, and the light in the particular wavelength range has a peak wavelength in the wavelength range of 400±10 nm, the wavelength range of 440±10 nm, the wavelength range of 470±10 nm, or the wavelength range of 600 nm or greater and 750 nm or less.

Appendix 12

The medical image processing apparatus wherein
the medical image is an inside-of-living-body image depicting an inside of a living body, and
the inside-of-living-body image has information on fluorescent light emitted by a fluorescent substance in the living body.

Appendix 13

The medical image processing apparatus wherein the fluorescent light is obtained by irradiating the inside of the living body with excitation light whose peak is 390 nm or greater and 470 nm or less.

Appendix 14

The medical image processing apparatus wherein
the medical image is an inside-of-living-body image depicting an inside of a living body, and
the particular wavelength range is a wavelength range of infrared light.

Appendix 15

The medical image processing apparatus wherein the particular wavelength range includes a wavelength range of 790 nm or greater and 820 nm or less or a wavelength range of 905 nm or greater and 970 nm or less, and the light in the particular wavelength range has a peak wavelength in the wavelength range of 790 nm or greater and 820 nm or less or the wavelength range of 905 run or greater and 970 nm or less.

Appendix 16

The medical image processing apparatus wherein
the medical image acquisition unit includes a special-light image acquisition unit that acquires a special-light image having information on the particular wavelength range, based on a normal-light image obtained by radiating light in a white range or light in a plurality of wavelength ranges as the light in the white range, and
the medical image is the special-light image.

Appendix 17

The medical image processing apparatus wherein a signal of the particular wavelength range is obtained through computation based on color information of red, green, and blue (RGB) or cyan, magenta, and yellow (CMY) included in the normal-light image.

Appendix 18

The medical image processing apparatus further comprising:
a feature quantity image generation unit that generates a feature quantity image through computation based on at least one of a normal-light image or a special-light image, the normal-light image being an image obtained by radiating light in a white range or light in a plurality of wavelength ranges as the light in white range, the special-light image being an image obtained by radiating light in a particular wavelength range, wherein
the medical image is the feature quantity image.

Appendix 19

An endoscope apparatus comprising:
the medical image processing apparatus according to any one of appendices 1 to 18; and
an endoscope that radiates at least one of light in a white wavelength range or light in a particular wavelength range to acquire an image.

Appendix 20

A diagnosis assistance apparatus comprising the medical image processing apparatus according to any one of appendices 1 to 18.

Appendix 21

A medical work assistance apparatus comprising the medical image processing apparatus according to any one of appendices 1 to 18.
<Others>
The image processing method described above may be configured as a program causing a computer to implement individual steps, and may be configured as a non-transitory recording medium such as a compact disk-read only memory (CD-ROM) storing this program.

In the embodiments described above, for example, a hardware structure of a processing unit that executes various processes of the training data collection apparatus 80 is, for example, various processors cited below. The various processors include a central processing unit (CPU) which is a general-purpose processor that executes software (program) to function as various processing units, a graphics processing unit (GPU) which is a processor specialized for image processing, a programmable logic device (PLD), such as a field programmable gate array (FPGA), which is a processor whose circuitry is changeable after production, a dedicated electric circuit, such as an application specific integrated circuit (ASIC), which is a processor having circuitry designed specifically for executing specific processing, and the like.

One processing unit may be constituted by one of these various processors, or by two or more processors of the same kind or different kinds (for example, a plurality of FPGAs, a combination of a CPU and an FPGA, or a combination of a CPU and a GPU). In addition, a plurality of processing units may be constituted by one processor. Examples in which the plurality of processing units are constituted by one processor include a first configuration, as exemplified by computers such as a server and a client, in which a combination of one or more CPUs and software constitutes one processor and this processor functions as the plurality of processing units. The examples also include a second configuration, as exemplified by a system on chip (SoC) or the like, in which a processor that implements functions of the entire system including the plurality of processing units on a single integrated circuit (IC) chip is used. As described above, the various processing units are configured using one or more of the various processors in terms of the hardware structure.

Further, the hardware structure of these various processors is, more specifically, electric circuitry in which circuit elements such as semiconductor elements are combined.

The technical scope of the present invention is not limited to the scope described in the embodiments above. The configuration or the like in each of the embodiments can be appropriately combined with that of another embodiment within a range not departing from the gist of the present invention.

REFERENCE SIGNS LIST

10 endoscopic-image-based training system
20 hospital LAN
22 electronic medical chart system
24 pathology system
30 endoscopy department local LAN
32 endoscopy management report terminal
34 input device
36 display
38 video capturing terminal
40 endoscopy management server
42 endoscopy report
44 examination image
46 moving-image storing NAS
50 AI training LAN
52 AI engine
54 input unit
56 feature quantity extraction unit
58 discrimination unit
60 output unit
52 training data input unit
64 training unit
70 order gateway
72 pathology system gateway
74 AI training data output gateway
80 training data collection apparatus
82 accepting unit
83 coordinate reception unit
84 display control unit
86 associating unit
88 recording control unit
90 endoscope apparatus
91 endoscope
92 light source
93 camera
94 medical image processing apparatus
95 medical image acquisition unit
96 medical image analysis processing unit
97 medical image analysis result acquisition unit
100 endoscopy report creation screen
102 record case button
110 AI training image association screen
112 image display area
114 findings-diagnosis information display area
116-1 to 116-3 tab
118-1 to 118-10 examination image
120-1, 120-2 findings-diagnosis information
122-1, 122-2 identification information
124, 144 mouse pointer
126 copied image
128-1 to 128-3 additional information
130 right click menu
140 lesion position information input screen
142-1, 142-2 examination image
146, 148 guide line
150 quadrangle
152, 156 bounding box
154, 158 circular region
S10 to S60 each step of training method
S71 to S74 each step of lesion position information input method

What is claimed is:

1. A training data collection apparatus comprising:
a display control unit that causes one or a plurality of endoscopic images captured with an endoscope to be displayed in an image display area of a display device and that causes one or a plurality of pieces of findings-diagnosis information on a lesion to be displayed in a findings-diagnosis information display area of the display device;
an accepting unit that accepts an operation on an input device, the operation being an operation of selecting at least one endoscopic image from among the endoscopic images displayed in the image display area and a piece of findings-diagnosis information relating to the at least one endoscopic image from among the pieces of findings-diagnosis information displayed in the findings-diagnosis information display area;
an associating unit that associates the selected endoscopic image with the selected piece of findings-diagnosis information; and
a recording control unit that causes a recording apparatus to record therein, as training data for use in training of a model that discriminates a lesion from an endoscopic image, the endoscopic image and the piece of findings-diagnosis information associated with each other, wherein the display control unit classifies endoscopic images associated with the respective pieces of findings-diagnosis information by the associating unit, into corresponding groups of the respective pieces of findings-diagnosis information and causes the endoscopic images to be displayed and switched on a group-by-group basis by using tabs.

2. The training data collection apparatus according to claim 1, wherein the accepting unit accepts an operation, on the input device, of selecting one of the tabs, and the display control unit causes an endoscopic image classified into a group corresponding to the selected tab to be displayed in the image display area.

3. The training data collection apparatus according to claim 1, wherein the display control unit classifies all selectable endoscopic images into a single group.

4. The training data collection apparatus according to claim 1, wherein the accepting unit accepts an operation of dragging and dropping at least one endoscopic image among the endoscopic images displayed in the image display area onto a piece of findings-diagnosis information displayed in the findings-diagnosis information display area, and the associating unit associates the dragged and dropped endoscopic image with the piece of findings-diagnosis information.

5. The training data collection apparatus according to claim 1, wherein the accepting unit accepts an operation of dragging and dropping at least one piece of findings-diagnosis information among the pieces of findings-diagnosis information displayed in the findings-diagnosis information display area onto an endoscopic image displayed in the image display area, and the associating unit associates the dragged and dropped piece of findings-diagnosis information with the endoscopic image onto which the piece of findings-diagnosis information is dropped.

6. The training data collection apparatus according to claim 1, wherein the display control unit causes identification information indicating the piece of findings-diagnosis information associated with the endoscopic image to be displayed along with the endoscopic image in the image display area.

7. The training data collection apparatus according to claim 6, wherein the display control unit causes the identification information to be displayed at a corresponding one of the tabs.

8. The training data collection apparatus according to claim 6, wherein the identification information is a number corresponding to the piece of findings-diagnosis information.

9. The training data collection apparatus according to claim 6, wherein the display control unit causes the identification information to be displayed along with the piece of findings-diagnosis information in the findings-diagnosis information display area.

10. The training data collection apparatus according to claim 1, wherein the display control unit causes the selected images to be displayed in an overlapping manner.

11. The training data collection apparatus according to claim 1, wherein the accepting unit accepts an operation of designating position information of a lesion contained in the endoscopic image, and the recording control unit causes the recording apparatus to record therein the designated position information as the training data.

12. The training data collection apparatus according to claim 11, wherein the accepting unit accepts a first position that is an upper left position of a quadrangular region containing the lesion and a second position that is a lower right position of the quadrangular region and is at a diagonal position of the first position.

13. The training data collection apparatus according to claim 12, wherein the accepting unit is a touch panel, the first position is a position where a user touches the touch panel, and the second position is a position where a finger of the user is separated from the touch panel after the finger is moved from the first position while keeping the finger in contact with the touch panel.

14. The training data collection apparatus according to claim 12, wherein in a case where the accepting unit accepts the position information of the lesion, the display control unit causes the position information of the lesion to be displayed in an endoscopic image other than the endoscopic image in which the position information of the lesion is designated.

15. The training data collection apparatus according to claim 12, comprising an output unit configured to output training data recorded in the recording apparatus, wherein the output unit determines the training data to be output based on an area calculated from the position information of the lesion.

16. A training system comprising:

a display device;

an input device;

a recording apparatus;

the training data collection apparatus according to claim 1; and a discriminator that discriminates a lesion from an endoscopic image by using a model, wherein the model is trained using the training data.

17. A trained model that has been trained by the training system according to claim 16.

18. An endoscopic image processing apparatus that analyzes an endoscopic image by using the trained model according to claim 17.

19. A training data collection method comprising:

a display control step of causing one or a plurality of endoscopic images captured with an endoscope to be displayed in an image display area of a display device and causing one or a plurality of pieces of findings-diagnosis information on a lesion to be displayed in a findings-diagnosis information display area of the display device;

an accepting step of accepting an operation on an input device, the operation being an operation of selecting at least one endoscopic image from among the endoscopic images displayed in the image display area and a piece of findings-diagnosis information relating to the at least one endoscopic image from among the pieces of findings-diagnosis information displayed in the findings-diagnosis information display area;

an association step of associating the selected endoscopic image with the selected piece of findings-diagnosis information; and a recording control step of causing a recording apparatus to record therein, as training data for use in training of a model that discriminates a lesion from an endoscopic image, the endoscopic image and the piece of findings-diagnosis information associated with each other, wherein the display control step classifies endoscopic images associated with the respective pieces of findings-diagnosis information in the association step, into corresponding groups of the respective pieces of findings-diagnosis information and causes the endoscopic images to be displayed and switched on a group-by-group basis by using tabs.

20. A non-transitory computer-readable recording medium that records thereon instructions which cause a computer to execute the training data collection method according to claim 19 when the instructions stored on the recording medium are read by the computer.

* * * * *